US009777295B2

(12) United States Patent
Botes et al.

(10) Patent No.: US 9,777,295 B2
(45) Date of Patent: Oct. 3, 2017

(54) METHODS FOR BIOSYNTHESIS OF ISOBUTENE

(71) Applicant: INVISTA North America S.á r.l., Wilmington, DE (US)

(72) Inventors: Adriana Leonora Botes, Rosedale East (GB); Alex Van Eck Conradie, Eaglescliffe (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 14/092,115

(22) Filed: Nov. 27, 2013

(65) Prior Publication Data

US 2014/0186913 A1    Jul. 3, 2014

Related U.S. Application Data

(60) Provisional application No. 61/730,549, filed on Nov. 28, 2012.

(51) Int. Cl.
 *C12Q 1/32* (2006.01)
 *C12P 5/02* (2006.01)
 *A61K 38/00* (2006.01)

(52) U.S. Cl.
 CPC ............. *C12P 5/026* (2013.01); *Y02E 50/343* (2013.01)

(58) Field of Classification Search
 CPC ...................................... C12P 5/026
 See application file for complete search history.

(56) References Cited

U.S. PATENT DOCUMENTS

| 8,703,455 B2 | 4/2014 | Marliere |
| 8,741,612 B2 | 6/2014 | Campbell et al. |
| 2011/0165644 A1 | 7/2011 | Marliere |
| 2011/0300597 A1 | 12/2011 | Burk et al. |
| 2012/0021478 A1 | 1/2012 | Osterhout et al. |
| 2012/0122563 A1 | 5/2012 | Walker et al. |
| 2012/0225466 A1 | 9/2012 | Burk et al. |
| 2013/0189753 A1 | 7/2013 | Pearlman et al. |
| 2013/0210104 A1 | 8/2013 | Pearlman et al. |
| 2013/0309742 A1 | 11/2013 | Campbell et al. |
| 2014/0065686 A1 | 3/2014 | Marliere |
| 2014/0141482 A1 | 5/2014 | Pearlman et al. |
| 2015/0037860 A1 | 2/2015 | Botes et al. |
| 2015/0079654 A1 | 3/2015 | Botes et al. |

FOREIGN PATENT DOCUMENTS

| EP | 2336340 | 6/2011 |
| EP | 2336341 | 6/2011 |
| WO | WO2009/155382 | 12/2009 |
| WO | WO2010/099201 | 9/2010 |
| WO | WO2010001078 A4 | 9/2010 |
| WO | WO 2011/011689 | 1/2011 |
| WO | WO 2011/076261 | 6/2011 |
| WO | WO 2011/076689 | 6/2011 |
| WO | WO 2011/076691 | 6/2011 |
| WO | WO 2011/079314 | 6/2011 |
| WO | WO2011/140171 | 11/2011 |
| WO | WO2012/018624 | 2/2012 |
| WO | WO 2012/052427 | 4/2012 |
| WO | WO2012/174439 | 12/2012 |
| WO | WO 2013/007786 | 1/2013 |
| WO | WO 2013/020118 | 2/2013 |
| WO | WO 2013/028519 | 2/2013 |
| WO | WO 2013/040383 | 3/2013 |
| WO | WO2013036812 A1 | 3/2013 |
| WO | WO 2013/057194 | 4/2013 |
| WO | WO2013/082542 | 6/2013 |
| WO | WO 2013/090915 | 6/2013 |
| WO | WO 2013/092567 | 6/2013 |
| WO | WO 2013/150100 | 10/2013 |
| WO | WO 2013/173437 | 11/2013 |
| WO | WO 2013/181647 | 12/2013 |
| WO | WO 2013/192183 | 12/2013 |
| WO | WO 2014/001517 | 1/2014 |
| WO | WO 2014/033129 | 3/2014 |
| WO | WO2013188546 A3 | 3/2014 |
| WO | WO 2014/064198 | 5/2014 |
| WO | WO 2014/085612 | 6/2014 |
| WO | WO 2014/015210 | 11/2014 |

OTHER PUBLICATIONS

Microbiology (2017) www.britannica.com/science/microbiology, pp. 1-8.*
Barta et al., "Structural basis for nucleotide binding and reaction catalysis in mevalonate diphosphate decarboxylase," Biochemistry, 51(28):5611-5621, Epub Jul. 6, 2012.
Brodkorb et al., "Linalool dehydratase-isomerase, a bifunctional enzyme in the anaerobic degradation of monoterpenes," *J Biol Chem.*, 285(40):30436-30442, Epub Jul. 27, 2010.

(Continued)

*Primary Examiner* — Anand Desai
*Assistant Examiner* — Samuel Liu
(74) *Attorney, Agent, or Firm* — Licata & Tyrrell P.C.

(57) ABSTRACT

The document provides methods for biosynthesizing isobutene using one or more isolated enzymes such as one or more of an enoyl-CoA dehydratase, a 2-hydroxyacyl-CoA dehydratase, an isovaleryl-CoA/acyl-CoA dehydrogenase and a mevalonate diphosphate decarboxylase, or using recombinant host cells expressing one or more such enzymes.

9 Claims, 9 Drawing Sheets

(56) References Cited

OTHER PUBLICATIONS

Buckel et al., "Glutaconate CoA-transferase from Acidaminococcus fermentans," *Eur J Biochem.*, 118(2):315-321, Aug. 1981.
Chayabutra and Ju, "Degradation of n-hexadecane and its metabolites by Pseudomonas aeruginosa under microaerobic and anaerobic denitrifying conditions," *Appl Environ Microbiol.*, 66(2):493-498, Feb. 2000.
Chung and Rhee, "Overexpression of the (R)-specific enoyl-CoA hydratase gene from Pseudomonas chlororaphis HS21 in Pseudomonas strains for the biosynthesis of polyhydroxyalkanoates of altered monomer composition," Biosci. Biotechnol. Biochem., 76(3): 613-616, 2012.
Dhe-Paganon et al., "Mechanism of mevalonate pyrophosphate decarboxylase: evidence for a carbocationic transition state," *Biochemistry*, 33(45):13355-13362, Nov. 15, 1994.
Eikmanns and Buckel, "Crystalline green 5-hydroxyvaleryl-CoA dehydratase from Clostridium aminovalericum," *Eur. J. Biochem.*, 197(3):661-668, May 8, 1991.
Ferrandez et al., "Genetic characterization and expression in heterologous hosts of the 3-(3-hydroxyphenyl)propionate catabolic pathway of Escherichia coli K-12," *J. Bacteriol.*, 179(8): 2573-2581, Apr. 1997.
Gogerty and Bobik, "Formation of isobutene from 3-hydroxy-3-methylbutyrate by diphosphomevalonate decarboxylase," *Appl Environ Microbiol.*, 76(24):8004-8010, Epub Oct. 22, 2010.
Guan et al., "Cytochrome P450-dependent desaturation of lauric acid: isoform selectivity and mechanism of formation of 11-dodecenoic acid," *Chem Biol Interact.*, 110(1-2):103-121, Mar. 1998.
He and Spain, "A novel 2-aminomuconate deaminase in the nitrobenzene degradation pathway of Pseudomonas pseudoalcaligenes JS45," *J Bacteriol.*, 180(9):2502-2506, May 1998.
International Preliminary Report on Patentability and Written Opinion for PCT/US2012/042757, issued Dec. 17, 2013, 7 pages.
International Preliminary Report on Patentability and Written Opinion for PCT/US2012/064407, issued May 13, 2014, 8 pages.
International Preliminary Report on Patentability and Written Opinion for PCT/US2012/067463, issued Jun. 3, 2014, 12 pages.
International Search Report in Application No. PCT/US2012/042757 dated Mar. 6, 2013, 5 pages.
International Search Report in Application No. PCT/US2012/064407, dated Feb. 7, 2013, 13 pages.
International Search Report in Application No. PCT/US2012/067463, dated Jun. 17, 2013, 19 pages.
International Search Report and Written Opinion in Application No. PCT/US2013/045430, dated Feb. 3, 2014, 20 pages.
Invitation to pay additional fees and, where applicable, protest fee for PCT/US2012/067463, dated Mar. 13, 2013, 17 pages.
Invitation to pay additional fees and, where applicable, protest fee for PCT/US2013/045430, dated Nov. 25, 2013, 6 pages.
Jang et al., "Bio-based production of C2-C6 platform chemicals," *Biotechnol Bioeng.*, 109(10):2437-2459, Epub Jul. 13, 2012.
Kasai et al., "Uncovering the protocatechuate 2,3-cleavage pathway genes," *J Bacteriol.*, 191(21):6758-6768, Epub Aug. 28, 2009.
Kim et al., "An allylic ketyl radical intermediate in clostridial amino-acid fermentation," *Nature.*, 452(7184):239-242, Mar. 2008.
Kim, "On the enzymatic mechanism of 2-hydroxyisocaproyl-CoA dehydratase from Clostridium difficile," 2004, Ph.D. dissertation, Philipps-Universität, Marburg, 2004.
Kizer et al., "Application of Functional Genomics to Pathway Optimization for Increased Isoprenoid Production," *Applied and Environmental Microbiology*, 2008, 74(10):3229-3241.
Kuzma et al., "Bacteria produce the volatile hydrocarbon isoprene," *Curr Microbiol.*, 30(2):97-103, Feb. 1995.
Kuzuyama, "Mevalonate and nonmevalonate pathways for the biosynthesis of isoprene units," *Biosci Biotechnol Biochem.*, 66(8):1619-1627, Aug. 2002.

Li et al., "Cupriavidus necator JMP134 rapidly reduces furfural with a Zn-dependent alcohol dehydrogenase," Biodegradation, 22(6): 1215-1225, Nov. 2011.
Liu et al., "Microbial production of R-3-hydroxybutyric acid by recombinant E. coli harboring genes of phbA, phbB, and tesB," *Appl Microbiol Biotechnol.*, 76(4):811-818, Epub Jul. 4, 2007.
Luo et al., "Production of 3-hydroxypropionic acid through propionaldehyde dehydrogenase PduP mediated biosynthetic pathway in Klebsiella pneumoniae," *Bioresour Technol.*, 103(1):1-6, Epub Oct. 2, 2011.
Mo et al., "Biosynthesis of the allylmalonyl-CoA extender unit for the FK506 polyketide synthase proceeds through a dedicated polyketide synthase and facilitates the mutasynthesis of analogues," *J Am Chem Soc.*, 133(4):976-985, Epub Dec. 22, 2010 [author manuscript].
Morrone et al., "Increasing diterpene yield with a modular metabolic engineering system in *E. coli*: comparison of MEV and MEP isoprenoid precursor pathway engineering," *Applied Microbiology and Biotechnology*, 2010, 85:1893-1906.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7," *Appl Environ Microbiol.*, 69(3):1564-1572, Mar. 2003.
Prather et al., "De nova biosynthetic pathways: rational design of microbial chemical factories," 2008, 19:468-474.
Bettie et al., "CYP4 Isozyme Specificity and the Relationship between ω-Hydroxylation and Terminal Desaturation of Valproic Acid," Biochemistry, 34(24): 7889-7895 (1995).
Schäfer et al., "Synthesis of short-chain diols and unsaturated alcohols from secondary alcohol substrates by the Rieske nonheme mononuclear iron oxygenase MdpJ.," Appl Environ Microbiol., 78(17):6280-6284, Epub Jun. 29, 2012.
Scherf and Buckel, "Purification and properties of an iron-sulfur and FAD-containing 4-hydroxybutyryl-CoA dehydratase/vinylacetyl-CoA delta 3-delta 2-isomerase from Clostridium aminobutyricum," *Eur J Biochem.*, 215(2):421-429, Jul. 15, 1993.
Scherf et al., "Succinate-ethanol fermentation in Clostridium kluyveri: purification and characterisation of 4-hydroxybutyryl-CoA dehydratase/vinylacetyl-CoA delta 3-delta 2-isomerase," *Arch Microbiol.*, 161(3):239-245, 1994.
Silver and Fall, "Characterization of aspen isoprene synthase, an enzyme responsible for leaf isoprene emission to the atmosphere," *J Biol Chem.*, 270(22):13010-13016, Jun. 2, 1995.
Sweeney et al., "Physiologically based pharmacokinetic modeling of 1,3-butadiene, 1,2-epoxy-3-butene, and 1,2:3,4-diepoxybutane toxicokinetics in mice and rats," *Carcinogenesis.*, 18(4):611-625, Apr. 1997.
Tseng et al., "Biosynthesis of chiral 3-hydroxyvalerate from single propionate-unrelated carbon sources in metabolically engineered *E. coli,*" *Microb Cell Fact.*, 9:96, Nov. 27, 2010.
Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," *Int J Biol Macromol.*, 31(4-5):195-205, Jan. 2003.
Ulmer et al., "Bacterial production of poly(.beta.-hydroxyalkanoates) containing unsaturated repeating units by Rhodospirillum rubrum," Macromolecules, 27(7):1675-1679, 1994.
Uniprot Accession No. B8ZLF3, Jun. 15, 2010, 2 pages.
Uniprot Accession No. P32377, Jun. 15, 2010, 4 pages.
Uniprot Accession No. Q7CCL9, Jun. 15, 2010, 2 pages.
Upton and Mckinney, "Role of the methylcitrate cycle in propionate metabolism and detoxification in *Mycobacterium smegmatis,*" *Microbiology*, 153(Pt 12):3973-3982, Dec. 2007.
Wang and Liao, "Alteration of product specificity of Rhodobacter sphaeroides phytoene desaturase by directed evolution," *J Biol Chem.*, 276(44):41161-41164, Epub Aug. 28, 2001.
Wendt et al., "Crystal structure of the carboxyltransferase subunit of the bacterial sodium ion pump glutaconyl-coenzyme A decarboxylase," *EMBO J.*, 22(14):3493-3502, Jul. 15, 2003.

(56) References Cited

OTHER PUBLICATIONS

White, "Butadiene production process overview," *Chem Biol Interact.*, 166(1-3):10-14, Epub Jan. 26, 2007.
Yang et al., "Enhancing production of bio-isoprene using hybrid MVA pathway and isoprenesynthase in *E. coli*," *PLoS One,* Apr. 2012, 7:1-7.
Zhao et al., "Biosynthesis of isoprene in *Escherichia coli* via methylerythritol phosphate (MEP) pathway," *Applied Microbilogy and Biotechnology,* Apr. 2011, 90:1915-1922.
Authorized officer Veronique Cornudet, International Search Report/Written Opinion in PCT/US2013/072275 dated Mar. 6, 2014, 12 pages.
Becker et al., "Metabolic flux engineering of L-lysine production in Corynebacterium glutamicum—over expression and modification of G6P dehydrogenase," J Biotechnol, 2007, 132(2):99-109, 11 pages.
Brigham et al., "Engineering Ralstonia eutropha for Production of Isobutanol from Co2, H2, and O2," Advanced Biofuels and Bioproducts, 2012, Chapter 39, 1065-1090, 36 pages.
Buckel et al., "2-Hydroxyacyl-CoA dehydratases, a novel family of molybdenum enzymes," J Inorganic Biochemistry, 2003, 96(1):53, 1 page.
Bugg et al., "The emerging role for bacteria in lignin degradation and bio-product formation," Current Opinion in Biotechnology, 2011, 22(3):394-400, 7 pages.
Foster-Fromme et al., "Biochemical characterization of isovaleryl-CoA dehydrogenase (LiuA) of Pseudomonas aeruginosa and the importance of liu genes for a functional catabolic pathway of methyl-branched compounds," FEMS Microbiol Lett, 2008, 286(1):78-84, 7 pages.
Genbank accession No. AAD44196.1, Oct. 15, 1999, 1 page.
Genbank accession No. AAG05403.1, Jan. 31, 2014, 2 pages.
Genbank accession No. AAV40818.1, Feb. 4, 2005, 1 page.
Genbank accession No. AAV40819.1, Feb. 4, 2005, 1 page.
Genbank accession No. AAV40820.1, Feb. 4, 2005, 1 page.
Genbank accession No. BAA21816.1, Aug. 19, 1997, 2 pages.
Genbank accession No. BAA92740, Aug. 1, 2007, 2 pages.
Genbank accession No. CAA32465.1, Jul. 26, 1995, 1 page.
Genbank accession No. CAA32466.1, Jul. 26, 1995, 1 page.
Genbank accession No. CAA42196.1, Oct. 16, 1995, 1 page.
Genbank accession No. CAA99573.1, Nov. 14, 2006, 2 pages.
Genbank accession No. NP_746661, Jun. 27, 2013, 2 pages.
Hermann et al., "Industrial production of amino acids by coryneform bacteria," J Biotechnol, 2003, 104(1-3):155-172, 18 pages.
Jaremko et al., "The initial metabolic conversion of levulinic acid in Cupriavidus necator," J Biotechnol, 2011, 155(3):293-298, 6 pages.
Kim et al., "Dehydration of ®-2-hydro9xyacyl-CoA to enoyl-CoA in the fermentation of a-amino acids by anaerobic bacteria," FEMS Microbiol Rev, 2004, 28(4):455-468, 14 pages.
Köpke et al., "2,3-Butanediol production by acetogenic bacteria, an alternative route to chemical synthesis, using industrial waste gas," App Environ Microbiol, 2011, 77(15):5467-5475, 9 pages.
Lan et al., "ATP drives direct photosynthetic production of 1-butanol in cyanobacterial," PNAS, 2012, 109(16):6018-6023, 6 pages.
Lee et al., "Conversion of beta-methylbutyric acid to beta-hydroxy-beta-methylbutyric acid by Galactomyces reessii," Appl Environ Microbiol, 1997, 63(11):4191-4195, 5 pages.
Lee et al., "Synthesis of pure meso-2,3-butanediol from crude glycerol using an engineered metabolic pathway in *Escherichia coli*," Appl Biochem Biotechnol, 2012, 166(7):1801-1813, 13 pages.
Li et al., "JMP134 rapidly reduces furfural with a Zn-dependent alcohol dehydrogenase," Biodegradation, 2011, 22(6):1215-1225, 11 pages.
Lim et al., "Amplification of the NADPH-Related Genes zwf and gnd for the Oddball Biosynthesis of PHBin an *E. coli* Tranformant Harboring a Cloned phbCAB Operon," J Bioscience and Bioengineering, 2002, 93(6):543-574, 7 pages.

Martin et al., "High-titer production of monomeric hydroxyl valerates from levulinic acid I Pseudomonas putida," J Biotechnol, 2009, 139(1):61-67, 7 pages.
Meijnen et al., "Improved p-hydroxybenzoate productoin by engineered Pseudomonas putida S12 by using a mixed-substrate feeding strategy," Appl Microbiol Biotechnol, 2011, 90(3):885-893, 9 pages.
Ohashi et al., "Continuous production of lactic acid from molasses by perfusion culture of Lactococcus lactis using a stirred ceramic membrane reactor," J Bioscience and Bioengineering, 1999, 87(5):647-654, 8 pages.
Papanikolaou et al., "Citric acid production by Yarrowia lipolytica cultivated on olive-mill wastewater-based media," Bioresour. Technol., 2008, 99(7):2419-2428, 10 pages.
Pérez-Pantoja et al., "Metabolic reconstruction of aromatic compounds degradation from the genome of the amazing pollutant-degrading bacterium Cupriavidus necator JMP134," FEMS Microbiol Rev., 2008, 32(5):736-794, 59 pages.
Prybylski et al., "Third-generation feed stocks for the clean and sustainable biotechnological production of bulk chemicals: synthesis of 2-hydroxyisobutyric acid," Energy, Sustainability and Society, 2012, 2:11, 9 pages.
Ramsay et al., "Use of a Nylon Manufacturing Waste as an Industrial Fermentation Substrate," Appl Environ Microbiol, 1986, 52(1):152-156, 5 pages.
Seedorf et al., "The genome of Clostridium kluyveri, a strict anaerobe with unique metabolic features," Proc Natl Acad Sci USA, 2008, 105(6):2128-2133, 6 pages.
Shen et al., "Driving Forces Enable High-Titer Anaerobic 1-Butanol Synthesis in *Escherichia coli*," Appl Environ Microbiol., 2011, 77(9):2905-2915, 11 pages.
Van Leeuwen et al., "Fermentative production of isobutene," Appl Microbiol Biotechnol, 2012, 93(4):1377-1387, 11 pages.
Wee et al., "Biotechnological production of lactic acid and its recent applications," Food Technol. Biotechnol., 2006, 44(2):163-172, 10 pages.
Yang et al., "Value-added uses for crude glycerol-a byproduct of biodiesel production," Biotechnology for Biofuels, 2012, 5:13, 10 pages.
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, 1999, 145(9):2323-2334, 12 pages.
Zhuang et al., "Divergence of function in the Hotdog-fold enzyme superfamily: the bacterial thioesterase YciA," Biochemistry, 2008, 47(9):2789-2796, 8 pages.
"Production of butadiene," China Synthetic Rubber Industry, Special issue of 1978, 21 pages (with partial English translation).
U.S. Non-Final Office Action in U.S. Appl. No. 13/916,156, dated Jul. 14, 2015, 35 pages.
U.S. Non-Final Office Action in U.S. Appl. No. 13/524,973, dated Jul. 23, 2015, 24 pages.
Daniel et al., "Biochemistry of coenzyme B12-dependent glycerol and diol dehydratases and organization of the encoding genes," 1999, FEMS Microbiology Reviews, 22: 553-566.
Fukui et al., "Expression and characterization of (R)-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. of Biological Chem., 2011, 186(16):14445-14454.
Genbank accession No. E1XUJ2.1. Sep. 5, 2012, 2 pages.
Gu et al., "Polyketide Decarboxylative chain Termination Preceded by O-sulfonation in curacin A Biosynthesis," J. Am. Chemical Soc., Nov. 2009, 131(44):16033-16035.
International Preliminary Report on Patentability in International Application No. PCT/US2013/045430, dated Dec. 16, 2014, 12 pages.
International Preliminary Report on Patentability and Written Opinion for PCT/US2013/072275, issued Jun. 2, 2015, 8 pages.

(56) References Cited

OTHER PUBLICATIONS

International Search Report and Written Opinion in Application No. PCT/US2014/048606, dated Oct. 31, 2014, 19 pages.

International Search Report and Written Opinion in Application No. PCT/US2014/049807, dated Nov. 5, 2014, 56 pages.

Jin et al., "The selective addition of water to C=C bonds; enzymes are the best chemists," Chem Commun., 2011, 47:2502-2510.

Kelada et al., "Delta-aminolevulinic acid dehydratase genotype and lead toxicity: A Huge Review," Am. J. Epidemiology, 2001, 154(1)1-13.

Luddeke et al. "Geraniol and Geranial Dehydrogenases Induced in Anaerobic Monoterpene Degradation by Castellaniella defragrans," Appl. and Environmental Microbiology, 2012, 78(7):2128-2136.

Luddeke et al.," Enantiospecific (S)-(+)-linalool formation from beta-myrcene by linalool dehydratase-isomerase," Z Naturforsch C., Jul./Aug. 2011, 66(7-8):409-412.

Martin et al., "Engineering a mevalonate pathway in *Escherichia coli* for production of terpenoids," Nature Biothechnology, Jul. 2003, 21(7):796-802.

McCarthy et al., "Structural basis of functional group activation by sulfotransferases in complex metabolic pathways," ACS Chem. Biol., 2012, 7:1994-2003.

Rude et al., "Terminal olefin (1-alkene) biosynthesis by a novel p450 fatty acid decarboxylase from Jeotgalicoccus speciesm," Appl. Environ. Microbiol., 2011, 77(5):1718-1727.

Toraya, "Radical catalysis of B12 enzymes: structure, mechanism, inactivation and reactivation of diol and glycerol dehydratases," Cellular and Molecular Life Sciences, 2000, 57:106-127.

Uniprot Accession No. I3RA72, Sep. 5, 2012, 2 pages.

U.S. Final Office Action in U.S. Appl. No. 13/691,623, dated Dec. 9, 2014, 15 pages.

U.S. Final Office Action in U.S. Appl. No. 13/524,973, dated Dec. 22, 2014, 24 pages.

U.S. Non-Final Office Action in U.S. Appl. No. 13/691,623, dated Jun. 25, 2014, 13 pages.

U.S. Non-Final Office Action in U.S. Appl. No. 13/524,973, dated Jun. 11, 2014, 17 pages.

International Search Report and Written Opinion in Application No. PCT/US2014/049786, dated Sep. 11, 2015, 17 pages.

Chinese Office Action in Chinese Application No. 201280040122.2, dated Jul. 17, 2015, 7 pages.

\* cited by examiner (R)-specific enoyl-CoA hydratase from *Pseudomonas aeruginosa* (encoded by PhaJ1 gene) (GenBank: BAA92740)

```
  1 msqvqnipya elevgqkaey tssiaerdlq lfaavsgdrn pvhldaayaa ttqfkeriah
 61 gmlsgalisa aiatvlpgpg tiylgqtlrf trpvklgddl kvelevlekl pknrvrmatr
121 vfnqagkqvv dgeaeimape eklsvelael ppisig
```

(R)-specific enoyl-CoA hydratase from *Aeromonas punctata* (GenBank: BAA21816.1)

```
  1 msaqslevgq karlskrfga aevaafaals edfnplhldp afaattafer pivhgmllas
 61 lfsglgqql pgkgsiylgq slsfklpvfv gdevtaevev talredkpia tlttriftqg
121 galavtgeav vklp
```

Enoyl-CoA hydratase from *Pseudomonas putida* (GenBank: NP_746661)

```
  1 msqvtntpye alevgqkaey kksveerdiq lfaamsgdhn pvhldaefaa ksmfreriah
 61 gmfsgalisa avactlpgpg tiylgqqmsf qkpvkigdtl tvrleilekl pkfkvriatn
121 vynqndelvv ageaeilapr kqqtvelvsp pnfvas
```

(S)-specific enoyl-CoA hydratase from *Bacillus subtilis* (GenBank CAA99573.1)

MNAISLAVDQFVAVLTIHNPPANALSSRILEELSSCLDQCETDAGVRSIIHGEGRFFSA
GADIKEFTSLKGNEDSSLLAERGQQLMERIESFPKPIIAAIHGAALGGGLELAMACHIRI
AAEDAKLGLPELNLGIIPGFAGTQRLPRYVGTAKALELIGSGEPISGKEALDLGLVSIGA
KDEAEVIEKAKALAAKFAEKSPQTLASLLELLYSNKVYSYEGSLKLEAKRFGEAFESEDA
KEGIQAFLEKRKPQFKGE

FIG. 3

HadBC, Clostridium difficile, GenBank Accession No. AAV40819.1

MSEKKEARVVINDLLAEQYANAFKAKEEGRPVGWSTSVFPQELAEVFDLNVLYPENQAAG
VAAKKGSLELCEIAESKGYSIDLCAYARTNFGLLENGGCEALDMPAPDFLLCCNNICNQV
IKWYENISRELDIPLIMIDTTFNNEDEVTQSRIDYIKAQFEEAIKQLEIISGKKFDPKKF
EEVMKISAENGRLWKYSMSLPADSSPSPMNGFDLFTYMAVIVCARGKKETTEAFKLLIEE
LEDNMKTGKSSFRGEEKYRIMMEGIPCWPYIGYKMKTLAKFGVNMTGSVYPHAWALQYEV
NDLDGMAVAYSTMFNNVNLDRMTKYRVDSLVEGKCDGAFYHMNRSCKLMSLIQYEMQRRA
AEETGLPYAGFDGDQADPRAFTNAQFETRIQGLVEVMEERKKLNRGEI

HadBC, Clostridium difficile, GenBank Accession No. AAV40820.1

MEAILSKMKEVVENPNAAVKKYKSETGKKAIGCFPVYCPEEIIHAAGMLPVGIWGGQTEL
DLAKQYFPAFACSIMQSCLEYGLKGAYDELSGVIIPGMCDTLICLGQNWKSAVPHIKYIS
LVHPQNRKLEAGVKYLISEYKGVKRELEEICGYEIEEAKIHESIEVYNEHRKTMRDFVEV
AYKHSNTIKPSIRSLVIKSGFFMRKEEHTELVKDLIAKLNAMPEEVCSGKKVLLTGILAD
SKDILDILEDNNISVVADDLAQETRQFRTDVPAGDDALERLARQWSNIEGCSLAYDPKKK
RGSLIVDEVKKKDIDGVIFCMMKFCDPEEYDYPLVRKDIEDSGIPTLYVEIDQQTQNNEQ
ARTRIQTFAEMMSLA

HadI, Clostridium difficile, GenBank Accession No. AAV40818.1

MYTMGLDIGSTASKGVILKNGEDIVASETISSGTGTTGPSRVLEKLYGKTGLAREDIKKV
VVTGYGRMNYSDADKQISELSCHARGVNFIIPETRTIIDIGGQDAKVLKLDNNGRLLNFL
MNDKCAAGTGRFLDVMAKIIEVDVSELGSISMNSQNEVSISSTCTVFAESEVISHLSENA
KIEDIVAGIHTSVAKRVSSLVKRIGVQRNVVMVGGVARNSGIVRAMAREINTEIIVPDIP
QLTGALGAALYAFDEAKESQKEVKNI

FIG. 4

HgdAB, Acidaminococcus fermentans, GenBank Accession No. CAA32465.1

MPKTVSPGVQALRDVVEKVYRELREAKERGEKVGWSSSKFPCELAESFGLHVGYPENQAA
GIAANRDGEVMCQAAEDIGYDNDICGYARISLAYAAGFRGANKMDKDGNYVINPHSGKQM
KDANGKKVFDADGKPVIDPKTLKPFATTDNIYEIAALPEGEEKTRRQNALHKYRQMTMPM
PDFVLCCNNICNCMTKWYEDIARRHNIPLIMIDVPYNEFDHVNEANVKYIRSQLDTAIRQ
MEEITGKKFDEDKFEQCCQNANRTAKAWLKVCDYLQYKPAPFNGFDLFNHMADVVTARGR
VEAAEAFELLAKELEQHVKEGTTTAPFKEQHRIMFEGIPCWPKLPNLFKPLKANGLNITG
VVYAPAFGFVYNNLDELVKAYCKAPNSVSIEQGVAWREGLIRDNKVDGVLVHYNRSCKPW
SGYMPEMQRRFTKDMGIPTAGFDGDQADPRNFNAAQYETRVQGLVEAMEANDEKKGK

HgdAB, Acidaminococcus fermentans, GenBank Accession No. CAA32466.1

MAISALIEEFQKVSASPKTMLAKYKAQGKKAIGCLPYYVPEELVYAAGMVPMGVWGCNGK
QEVRSKEYCASFYCTIAQQSLEMLLDGTLDGLDGIITPVLCDTLRPMSQNFKVAMKDKMP
VIFLAHPQVRQNAAGKQFTYDAYSEVKGHLEEICGHEITNDAILDAIKVYNKSRAARREF
CKLANEHPDLIPASVRATVLRAAYFMLKDEYTEKLEELNKELAAAPAGKFDGHKVVVSGI
IYNMPGILKAMDDNKLAIAADDCAYESRSFAVDAPEDLDNGLQALAVQFSKQKNDVLLYD
PEFAKNTRSEHVCNLVKESGAEGLIVFMMQFCDPEEMEYPDLKKALDAHHIPHVKIGVDQ
MTRDFGQAQTALEAFAESL

HgdC, Acidaminococcus fermentans, GenBank Accession No. CAA42196.1

MSIYTLGIDVGSTASKCIILKDGKEIVAKSLVAVGTGTSGPARSISEVLENAHMKKEDMA
FTLATGYGRNSLEGIADKQMSELSCHAMGASFIWPNVHTVIDIGGQDVKVIHVENGTMTN
FQMNDKCAAGTGRFLDVMANILEVKVSDLAELGAKSTKRVAISSTCTVFAESEVISQLSK
GTDKIDIIAGIHRSVASRVIGLANRVGIVKDVVMTGGVAQNYGVRGALEEGLGVEIKTSP
LAQYNGALGAALYAYKKAAK

FIG. 4 (continued)

liuA, Pseudomonas aeruginosa PAO1, GenBank Accession No. AAG05403.1

MTYPSLNFALGETIDMLRDQVRGFVAAELQPRAAQIDQDNQFPMDMWRKFGEMGLLGITV
DEEYGGSALGYLAHAVMEEISRASASVALSYGAHSNLCVNQIKRNGNAEQKARYLPALV
SGEHIGALAMSEPNAGSDVVSMKLRADRVGDRFVLNGSKMWITNGPDAHTYVIYAKTDAD
KGAHGITAFIVERDWKGFSRGPKLDKLGMRGSNTCELIFQDVEVPEENVLGAVNGGVKVL
MSGLDYERVVLSGGPVGIMQACMDVVVPYIHDRRQFGQSIGEFQLVQGKVADMYTALNAS
RAYLYAVAAACDRGETTRKDAAGVILYSAERATQMALDAIQILGGNGYINEFPTGRLLRD
AKLYEIGAGTSEIRRMLIGRELFNETR

Streptomyces avermitilis acdH gene (GenBank Accession No. AAD44196.1

MDHRLTPELEELRRTVEEFAHDVVAPKIGDFYERHEFPYEIVREMGRMGLFGLPFPEEYG
GMGGDYLALGIALEELARVDSSVAITLEAGVSLGAMPIHLFGTDAQKAEWLPRLCSGEIL
GAFGLTEPDGGSDAGATRTTARLDESTNEWVINGTKCFITNSGTDITGLVTVTGRKP
DGKPLISSIIVPSGTPGFTVAAPYSKVGWNASDTRELSFADVRVPAANLLGEQGRGYAQF
LRILDEGRIAISALATGLAQGCVDESVKYAGERHAFGRNIGAYQAIQFKIADMEMKAHMA
RVGWRDAASRLVAGEPFKKEAAIAKLYSSTVAVDNAREATQIHGGYGFMNEYPVARMWRD
SKILEIGEGTSEVQRMLIARELGLVG
60893371.doc

FIG. 5

| Sample ID | Analyte | Mwt [g/mol] | Peak Retention Time (mins) [min] | Peak Area @ 260nm (mAu) [mAu] | Observed Mass (m/z) Negative mode (M-H) | Observed Mass (m/z) positive mode (M+H) | Comments |
|---|---|---|---|---|---|---|---|
| 0.1 [mg/mL] crotonyl CoA as standard | Crotonyl-CoA | 835.6 | 5.374 | 1839.89 | 833.7 | 835.9 | |
| Biotransformation at 1 [h] time point | 3-hydroxybutanoyl-CoA | 853.6 | 4.531 | 10197.8 | 851.9 | 854 | Biotransformation undertaken at 1 [mM] substrate concentration. |
| | Crotonyl-CoA | 835.6 | 5.37 | 907.59 | 833.9 | 836 | (m/z) corresponds to desired product. |
| Standard only control 1 [h] time point | 3-hydroxybutanoyl-CoA | 853.6 | 4.529 | 10571.9 | 865.9 | 868.1 | |
| | Crotonyl-CoA | 835.6 | 5.37 | 9.207 | 833.9 | 836 | Weak signal in baseline noise of MS. |

FIG. 7

| Sample ID | Analyte | Mwt [g/mol] | Peak Retention Time (mins) [min] | Peak Area @260nm (mAu) [mAu] | Observed Mass (m/z) Negative mode (M-H) | Observed Mass (m/z) Positive mode (M+H) | Comments |
|---|---|---|---|---|---|---|---|
| 2 [mM] reference standard | 3-methyl-3-hydroxy-butanoyl-CoA | 867.2 | 4.759 | 8596.83 | 865.9 | 868.1 | Acetyl-CoA impurity was formed during substrate preparation. |
| | acetyl-CoA | 809.6 | 4.502 | 5150.72 | 807.9 | 810 | |
| Biotransformation at 1 [h] time point | 3-methyl-3-hydroxy-butanoyl-CoA | 867.2 | 4.783 | 3697.66 | 865.9 | 868.1 | Biotransformation undertaken at 1 [mM] substrate concentration. |
| | acetyl-CoA | 809.6 | 4.519 | 2372.45 | 807.9 | 810 | |
| | 3-methyl-but-2-enoyl-CoA | 849.2 | 6.127 | 84.89 | 848 | 850 | (m/z) corresponds to desired product. |
| Substrate only control at 1 [h] time point | 3-methyl-3-hydroxy-butanoyl-CoA | 867.2 | 4.776 | 3623.56 | 865.9 | 868.1 | no peak/mass corresponding to product |
| | acetyl-CoA | 809.6 | 4.511 | 2275.27 | 807.9 | 810 | |

FIG. 8

METHODS FOR BIOSYNTHESIS OF ISOBUTENE

This application claims priority of U.S. Provisional Application Ser. No. 61/730,549, filed Nov. 28, 2012. The contents of the prior application is incorporated herein by reference in its entirety.

TECHNICAL FIELD

This document relates to methods for biosynthesizing isobutene using one or more isolated enzymes such as one or more of an enoyl-CoA dehydratase, a 2-hydroxyacyl-CoA dehydratase, an isovaleryl-CoA/acyl-CoA dehydrogenase, and a mevalonate diphosphate decarboxylase, or using recombinant host cells expressing one or more such enzymes.

BACKGROUND

Isobutene is an important monomer in the manufacture of fuel additives, butyl rubber polymer, and antioxidants (Bianca et al., *Appl. Microbiol. Biotechnol.*, 2012, 93, 1377-1387).

Manufacturers of goods using isobutene as feedstock depend on a number of petroleum-based sources, including (i) a C4 stream from a steam cracker separated from the butadiene, (ii) butene-butane fractions from a catalytic cracker and (iii) n-butane (from liquid petroleum gas) that is isomerized to isobutane and dehydrogenated to isobutene.

Given a reliance on petrochemical feedstocks and energy intensive processes, biotechnology offers an alternative approach via biocatalysis. Biocatalysis is the use of biological catalysts, such as enzymes or whole cells, to perform biochemical transformations of organic compounds.

Accordingly, against this background, it is clear that there is a need for sustainable methods for producing intermediates, in particular isobutene, wherein the methods are biocatalysis based. Both bioderived feedstocks and petrochemical feedstocks are viable starting materials for the biocatalysis processes.

The introduction of a double bond into a short branch chain aliphatic carbon substrate is a key consideration in synthesizing isobutene via a biocatalytic process. In this vain, a cytochrome P450 from *Rhodotorula minuta* var. *texensis* IFO 1102 forms isobutene via the decarboxylation of isovalerate. Also, it has been demonstrated that variants of oleate hydratase accept isobutanol and variants of mevalonate diphosphate decarboxylase accept 3-hydroxy-3-methylbutyrate as a substrate in the biosynthesis of isobutene. A number of enzymes have thus been identified as having catalytic activity in the synthesis of isobutene (Bianca et al., *Appl. Microbiol. Biotechnol.*, 2012, 93, 1377-1387).

However, the identified biochemical pathways leading to the precursors accepted for isobutene synthesis are carbon inefficient, reflected by low maximum theoretical yields on carbon. For example, the only pathways identified for exploiting the catalytic activity of mevalonate diphosphate decarboxylase have maximum theoretical yields of ~0.2 [(g isobutene)/(g glucose)] (Bianca et al., 2012, supra). The economical production of isobutene using mevalonate diphosphate decarboxylase as final enzymatic step is thus challenged by carbon yield limitations.

SUMMARY

This document is based, at least in part, on constructing carbon efficient biochemical pathways for producing 3-methyl-3-hydroxy-butanoate, which can be converted to isobutene by a mevalonate diphosphate decarboxylase. Such pathways can rely on a 2-hydroxyacyl-CoA dehydratase or an isovaleryl-CoA/acyl-CoA dehydrogenase, and an enoyl-CoA hydratase (e.g., a (R)-specific enoyl-CoA hydratase) in synthesizing 3-methyl-3-hydroxy-butanoate. Prior to the present invention, it was not known that 2-hydroxyacyl-CoA dehydratase or an isovaleryl-CoA dehydrogenase combined with an enoyl-CoA hydratase could be utilized for the biological synthesis of 3-methyl-3-hydroxy-butanoate, leading to the synthesis of isobutene. Also, prior to the present invention, it was not known that an enoyl-CoA hydratase of bacterial origin could be utilized to synthesize 3-methyl-3-hydroxy-butanoate, leading to the synthesis of isobutene.

Thus, this document provides pathways and enzymes which can convert either of the central precursors 3-methyl-2-oxobutanoate or 4-methyl-2-oxopentanoate into isobutene via a common intermediate, 3-methyl-3-hydroxy-but-2-enoyl-CoA. As used herein, the term "central precursor" is used to denote any metabolite in any metabolic pathway shown herein leading to the synthesis of isobutene. The term "central metabolite" is used herein to denote a metabolite that is produced in all microorganisms to support growth.

In one aspect, this document features a method for synthesizing isobutene. The method includes (i) dehydrating 3-methyl-2-hydroxy-butanoyl-CoA and hydrating 3-methyl-but-2-enoyl-CoA, and converting the resulting product to isobutene. A 2-hydroxyacyl-CoA dehydratase can dehydrate 3-methyl-2-hydroxy-butanoyl-CoA. The 2-hydroxyacyl-CoA dehydratase can be encoded by the gene products HadI and HadBC or encoded by the gene products HgdC and HgdAB. The 2-hydroxyacyl-CoA dehydratase can have at least 70% sequence identity to the amino acid sequences set forth in SEQ ID NOs. 5 and 6; or can have at least 70% sequence identity to the amino acid sequences set forth in SEQ ID NOs. 8 and 9. A (R)-specific enoyl-CoA hydratase or an (S)-specific enoyl-CoA hydratase can hydrate 3-methyl-but-2-enoyl-CoA. The (R)-specific enoyl-CoA hydratase can have at least 70% sequence identity to any one of the amino acid sequences set forth in SEQ ID NOs:1-3. The (S)-specific enoyl-CoA hydratase can have at least 70% sequence identity to the amino acid sequence set forth in SEQ ID NO:4.

This document also features a method for synthesizing isobutene. The method includes dehydrogenating 3-methyl-butanoyl-CoA and hydrating 3-methyl-but-2-enoyl-CoA, and converting the resulting product to isobutene. An isovaleryl-CoA or acyl-CoA dehydrogenase can dehydrogenate 3-methyl-butanoyl-CoA. The isovaleryl-CoA or acyl-CoA dehydrogenase can have at least 70% sequence identity to the amino acid sequence set forth in SEQ ID NO:11 or SEQ ID NO:12. A (R)-specific enoyl-CoA hydratase or an (S)-specific enoyl-CoA hydratase can hydrate 3-methyl-but-2-enoyl-CoA. The (R)-specific enoyl-CoA hydratase can have at least 70% sequence identity to any one of the amino acid sequences set forth in SEQ ID NOs:1-3. The (S)-specific enoyl-CoA hydratase can have at least 70% sequence identity to the amino acid sequence set forth in SEQ ID NO:4.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

In any the methods described herein, the method can be performed in a recombinant host (e.g., a prokaryote or eukaryote). The prokaryotic host can be from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia acidovorans*, from the genus *Bacillus* such as *Bacillus subtilis*; from the genes *Lactobacillus* such as *Lactobacillus delbrueckii*; from the genus *Lactococcus* such as *Lactococcus lactis* or from the genus *Rhodococcus* such as *Rhodococcus equi*. The eukaryotic host can be from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica* or from the genus *Issatchenkia* such as *Issathenkia orientalis* or from the genus *Debaryomyces* such as *Debaryomyces hansenii* or from the genus *Arxula* such as *Arxula adenoinivorans* or from the genus *Kluyveromyces* such as *Kluyveromyces lactis*.

In any the methods described herein, a fermentation strategy can be used that entails anaerobic, micro-aerobic or aerobic cultivation. A fermentation strategy can entail nutrient limitation such as nitrogen, phosphate or oxygen limitation. A cell retention strategy using a ceramic hollow fiber membrane can be employed to achieve and maintain a high cell density during fermentation. The principal carbon source fed to the fermentation can derive from a biological or non-biological feedstock. The biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue (NVR) or a caustic wash waste stream from cyclohexane oxidation processes.

In another aspect, this document features a recombinant host that includes an exogenous nucleic acid encoding a 2-hydroxyacyl-CoA dehydratase and an enoyl-CoA hydratase, the host producing isobutene. The host further can include a mevalonate diphosphate decarboxylase. The host further can include a (i) a 2-hydroxy-acyl dehydrogenase, (ii) a CoA transferase or a CoA-ligase, and (iii) a thioesterase.

In another aspect, this document features a recombinant host that includes an exogenous nucleic acid encoding an isovaleryl-CoA/acyl-CoA dehydrogenase and an enoyl-CoA hydratase, the host producing isobutene. The host further can include a mevalonate diphosphate decarboxylase. The host further can include a 4-methyl-2-oxo-pentanoate dehydrogenase complex and a thioesterase. The host further can include an indolepyruvate decarboxylase, a phenylacetaldehyde dehydrogenase, and a CoA-ligase.

In any of the recombinant hosts, the enoyl-CoA hydratase can be a (R)-specific enoyl-CoA hydratase having at least 70% sequence identity to any one of the amino acid sequences set forth in SEQ ID NOs:1-3 or a (S)-specific enoyl-CoA hydratase having at least 70% sequence identity to the amino acid sequence set forth in SEQ ID NO:4.

In any of the recombinant hosts, the host can naturally accumulate polyhydroxyalkanoates and comprise attenuated polymer synthase enzymes.

In any of the recombinant hosts, the host further can include one or more of the following attenuated enzymes: a phosphotransacetylase, an acetate kinase, an enzyme that degrades pyruvate to lactate, an enzyme that degrades phophoenolpyruvate to succinate, an enzyme degrading acetyl-CoA to ethanol, or the final branch chain amino acid transaminase.

In any of the recombinant hosts, the host further can overexpress a gene encoding one or more of the following: a puridine nucleotide transhydrogenase, a glyceraldehyde-3P-dehydrogenase, a malic enzyme, a glucose-6-phosphate dehydrogenase, a fructose 1,6 diphosphatase, or a feedback inhibition resistant mutant of an acetolactate synthase, wherein the acetolactate synthase is resistant to feedback inhibition by branch chain amino acids. The gene encoding the acetolactate synthase can be expressed using a promoter not subject to genetic repression by branch-chain amino acids.

In any of the recombinant hosts, the efflux of isobutene across the cell membrane can be enhanced or amplified by genetic engineering of the cell membrane or increases to an associated transporter activity for isobutene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIG. 3 contains the amino acid sequence of an (R)-specific enoyl-CoA hydratase from *Pseudomonas aeruginosa* (encoded by the PhaJ1 gene) (GenBank Accession No. BAA92740, SEQ ID NO:1); *Aeromonas punctata* (GenBank Accession No. BAA21816.1, SEQ ID NO:2); and *Pseudomonas putida* (GenBank Accession No. NP 746661, SEQ ID NO:3), and a (S)-specific enoyl-CoA hydratase from *Bacillus subtilis* (GenBank Accession No. CAA99573.1, SEQ ID NO:4).

FIG. 4 contains the amino acid sequence of a *Clostridium difficile* 2-hydroxyacyl-CoA dehydratase (encoded by a HadBC gene) (see GenBank Accession Nos. AAV40819.1 and AAV40820.1, SEQ ID NOs. 5 and 6, respectively) and a *Clostridium difficile* initiator (encoded by HadI) (GenBank Accession No. AAV40818.1, SEQ ID NO:7).

FIG. 4 also contains the amino acid sequence of an *Acidaminococcus fermentans* 2-hydroxyacyl-CoA dehydratase encoded by the HgdAB gene (see GenBank Accession Nos. CAA32465.1 and CAA32466.1, SEQ ID NOs: 8 and 9, respectively) and an *Acidaminococcus fermentans* initiator encoded by HdgC (see GenBank Accession No. CAA42196.1, SEQ ID NO:10).

FIG. 5 contains the amino acid sequence of a *Pseudomonas aeruginosa* PAUL isovaleryl-CoA dehydrogenase encoded by the liuA gene (GenBank Accession No. AAG05403.1, SEQ ID NO: 11) and the amino acid sequence of a *Streptomyces avermitilis* acyl-CoA dehydrogenase encoded by the acdH gene (GenBank Accession No. AAD44196.1, SEQ ID NO:12).

FIG. 7 is a table of results for the LC-MS analysis of an enzyme assay in the reverse (dehydrating) direction for an enoyl-CoA hydratase activity encoded by phaJ. The results indicate that the enoyl-CoA hydratase is reversible, favoring the forward hydration reaction.

FIG. 8 is a table of results for the LC-MS analysis of an enzyme assay in the reverse (dehydrating) direction for an enoyl-CoA hydratase encoded by phaJ. The results indicate that the enoyl-CoA hydratase accepted 3-methyl-3-hydroxybutanoyl-CoA as substrate. Given the reversibility of the enzyme reaction, the enoyl-CoA hydratase accepts 3-methyl-3-hydroxybut-2-enoyl-CoA as a substrate.

DETAILED DESCRIPTION

Figure 1:
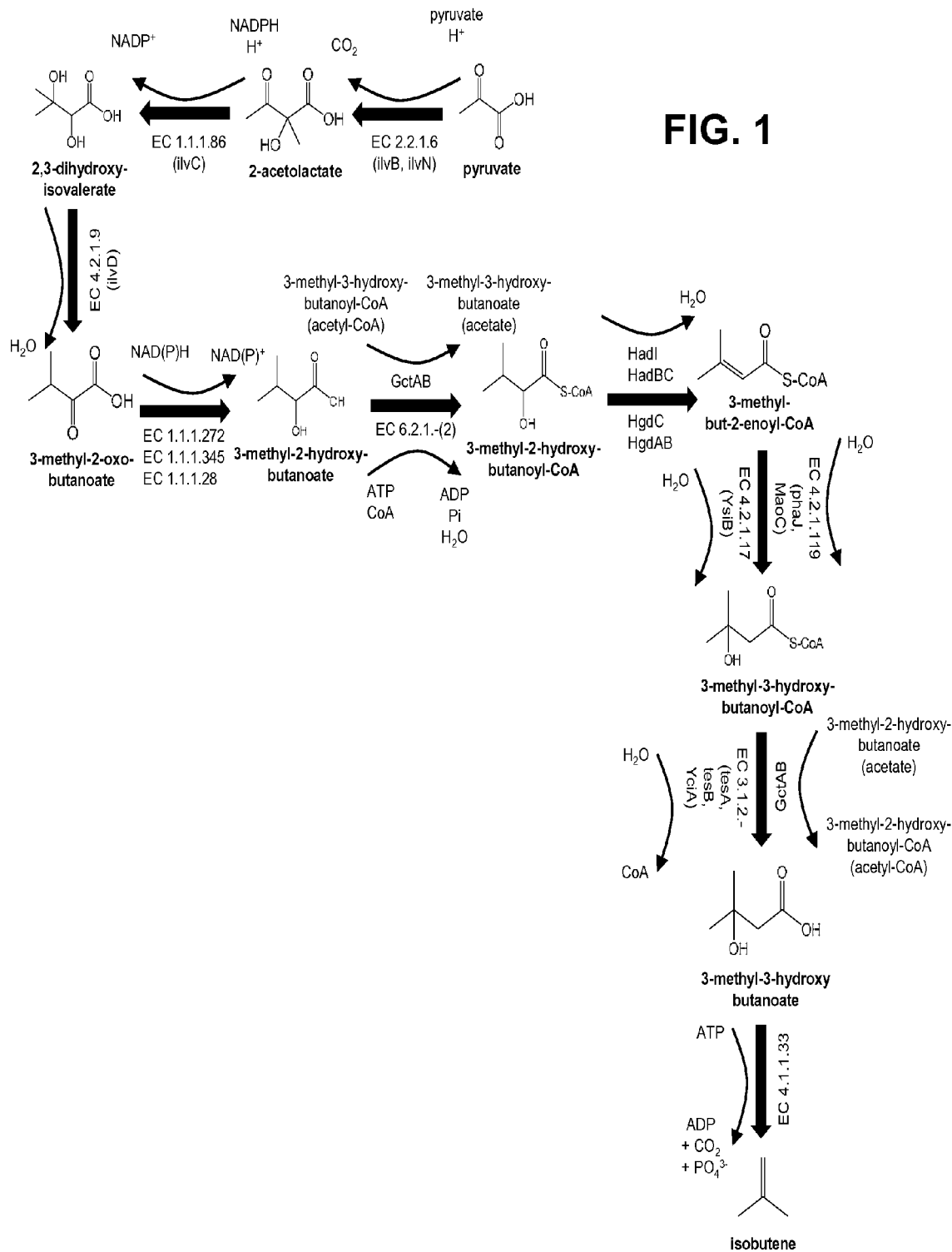
FIG. 1 is a schematic of exemplary biochemical pathway leading to isobutene using 3-methyl-2-oxobutanoate as a central precursor.

In particular, this document provides enzymes and recombinant host microorganisms for isobutene synthesis that can form a branch chain enoyl-CoA substrate, 3-methyl-but-2-enoyl-CoA, and hydrate the substrate to form 3-methyl-3-hydroxybutanoyl-CoA, which in turn can be converted after one or more enzymatic steps to isobutene by a mevalonate diphosphate decarboxylase. As such, host microorganisms described herein can include pathways that can be manipulated such that isobutene can be produced.

In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species, or can be from multiple sources, i.e., different species.

Nucleic acids encoding the enzymes described herein have been identified from various organisms and are readily available in publicly available databases such as GenBank or EMBL. Any of the enzymes described herein that can be used for isobutene production can have at least 70% sequence identity (homology) (e.g., at least 75%, 80%, 85%, 90%, 95%, 97%, 98%, 99%, or 100%) to the amino acid sequence of the corresponding wild-type enzyme. For example, an enoyl-CoA hydratase (e.g., a (R)-specific enoyl-CoA hydratase) described herein can have at least 70% sequence identity (homology) (e.g., at least 75%, 80%, 85%, 90%, 95%, 97%, 98%, 99%, or 100%) to the amino acid sequence of the *Pseudomonas aeruginosa* enoyl-CoA hydratase encoded by Pha II gene (GenBank Accession No. BAA92740, SEQ ID NO:1), *Aeromonas punctata* enoyl-CoA hydratase (GenBank Accession No. BAA21816.1, SEQ ID NO:2), or *Pseudomonas putida* enoyl-CoA hydratase (GenBank Accession No. NP 746661, SEQ ID NO:3). See, FIG. 3. An enoyl-CoA hydratase also can have at least 70% sequence identity (homology) (e.g., at least 75%, 80%, 85%, 90%, 95%, 97%, 98%, 99%, or 100%) to the amino acid sequence of the *Bacillus subtilis* (S)-specific enoyl CoA hydratase (GenBank Accession No. CAA99573.1, SEQ ID NO:4). See, FIG. 3.

For example, a 2-hydroxyacyl-CoA dehydratase described herein can have at least 70% sequence identity (homology) (e.g., at least 75%, 80%, 85%, 90%, 95%, 97%, 98%, 99%, or 100%) to the amino acid sequence of a *Clostridium difficile* 2-hydroxyacyl-CoA dehydratase encoded by a HadBC gene (see GenBank Accession Nos. AAV40819.1 and AAV40820.1, SEQ ID NOs. 5 and 6, respectively) and its *Clostridium difficile* initiator encoded by HadI (GenBank Accession No. AAV40818.1, SEQ ID NO:7). The HadBC gene encodes the two subunits of the dehydratase. For example, a 2-hydroxyacyl-CoA dehydratase described herein can have at least 70% sequence identity (homology) (e.g., at least 75%, 80%, 85%, 90%, 95%, 97%, 98%, 99%, or 100%) to the amino acid sequence of an *Acidaminococcus fermentans* 2-hydroxyacyl-CoA dehydratase encoded by the HgdAB gene (see GenBank Accession Nos. CAA32465.1 and CAA32466.1, SEQ ID NOs: 8 and 9, respectively) and its *Acidaminococcus fermentans* initiator encoded by HdgC (see GenBank Accession No. CAA42196.1, SEQ ID NO:10). The HgdAB gene encodes the two subunits of the dehydratase. See, FIG. 4.

For example, an isovaleryl-CoA dehydrogenase described herein can have at least 70% sequence identity (homology) (e.g., at least 75%, 80%, 85%, 90%, 95%, 97%, 98%, 99%, or 100%) to the amino acid sequence of a *Pseudomonas aeruginosa* PAO1 isovaleryl-CoA dehydrogenase encoded by the liuA gene (GenBank Accession No. AAG05403.1, SEQ ID NO: 11).

For example, an acyl-CoA dehydrogenase described herein can have at least 70% sequence identity (homology) (e.g., at least 75%, 80%, 85%, 90%, 95%, 97%, 98%, 99%, or 100%) to the amino acid sequence of a *Streptomyces avermitilis* acyl-CoA dehydrogenase encoded by the acdH gene (GenBank Accession No. AAD44196.1, SEQ ID NO: 12). See, FIG. 5.

The percent identity (homology) between two amino acid sequences can be determined as follows. First, the amino acid sequences are aligned using the BLAST 2 Sequences (B12seq) program from the stand-alone version of BLASTZ containing BLASTP version 2.0.14. This stand-alone version of BLASTZ can be obtained from Fish & Richardson's web site (worldwide web address fr.com/blast/) or the U.S. government's National Center for Biotechnology Information worldwide web address ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Recombinant hosts can naturally express none or some (e.g., one or more, two or more, three or more, four or more, five or more, or six or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, engineered cells, or engineered hosts. Thus, as described herein, recombinant hosts can include nucleic acids encoding one or more of a decarboxylase, a dehydrogenase, a hydratase, a thioesterase, a Coenzyme A ligase, or a Coenzyme A transferase, as described in more detail below.

For example, recombinant hosts can include an exogenous nucleic acid encoding a 2-hydroxyacyl-CoA dehydratase and an enoyl-CoA hydratase, or an isovaleryl-CoA/acyl-CoA dehydrogenase and an enoyl-CoA hydratase. Such hosts can produce isobutene and include a nucleic acid encoding a mevalonate diphosphate decarboxylase. The hosts further can include (i) a 2-hydroxy-acyl dehydrogenase, (ii) a CoA transferase or a CoA-ligase, and/or (iii) a thioesterase or a CoA transferase. In some embodiments, the hosts further can include (i) a 4-methyl-2-oxo-pentanoate dehydrogenase, (ii) an indolepyruvate decarboxylase, a phenylacetaldehyde dehydrogenase and a CoA-ligase and/or (iii) a thioesterase.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturallyoccurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In addition, the production of isobutene can be performed in vitro using the isolated enzymes described herein, using a lysate (e.g., a cell lysate) from a host microorganism as a source of the enzymes, or using a plurality of lysates from different host microorganisms as the source of the enzymes.

In some embodiments, 3-methyl-but-2-enoyl-CoA is formed by an isovaleryl-CoA or acyl-CodA dehydrogenase enzyme classified, for example, under EC 1.3.8.4, such as the gene product of liuA or acdH. The liuA gene from *Pseudomonas aeruginosa* has dehydrogenase activity specific for isovaleryl-CoA (see, for example, Foster-Fromme and Jendrossek, *FEMS Microbiol. Lett.*, 2008, 286, 78-84). The acdH gene from *Streptomyces avermitilis* also has dehydrogenase activity for isovaleryl-CoA (see, for example, Zhang et al., *Microbiology*, 1999, 145, 2323-2334).

In some embodiments, 3-methyl-but-2-enoyl-CoA is formed by a 2-hydroxyacyl-CoA dehydratase classified, for example, under EC 4.2.1.-, such as the product of the HadBC gene from *Clostridium difficile* and its initiator HadI (see FIG. 4), or the product of the HgdAB gene from *Acidaminococcus fermentans* and its initiator HdgC (see FIG. 4). In some embodiments, the 2-hydroxyacyl-CoA dehydratase is the result of enzyme engineering. The 2-hydroxyacyl-CoA dehydratase enzymes isolated from anaerobic bacteria possess a common catalytic mechanism employed in amino acid degradation pathways. For example, the gene products of HadBC/HadI from *Clostridium difficile* catalyse the conversion of (R)-2-hydroxyisocaproyl-CoA to isocaprenoyl-CoA. Similarly, the gene products of HgdAB/HdgC catalyse the conversion of 2-hydroxyglutaryl-CoA to glutaconyl-CoA (Kim et al., *FEMS Microbiol. Reviews*, 2004, 28, 455-468).

In some embodiments, the 3-hydroxy functional group is introduced into 3-methyl-but-2-enoyl-CoA by a R-specific enoyl-CoA hydratase enzyme classified, for example, under EC 4.2.119 such as the gene product of phaJ or MaoC or a bacterial (S)-specific enoyl-CoA hydratase classified, for example, under EC 4.2.1.17 such as the gene product of YsiB. In some embodiments, the enoyl-CoA hydratase enzyme is the result of enzyme engineering. A single enzyme candidate for the introduction of a 3-hydroxy functional group into 3-methylbuten-2-enoyl-CoA was identified in the cell free extract of *Galactomyces reessii*, containing an enoyl-CoA hydratase classified in EC 4.2.1.17 that converts 3-methylbuten-2-enoyl-CoA to 3-hydroxy-3-methylbutanoyl-CoA (Lee et al., *Appl. Environ. Microbiol.*, 1997, 63(11), 4191-4195). Until now, an equivalent enoyl-CoA hydratase activity from bacterial origin had not been identified.

In some embodiments, the hydratase enzyme can be the result of enzyme engineering, using the enzyme structure of phaJ, EC 4.2.1.119 and EC 4.2.1.17 to inform rational enzyme design.

In some embodiments (FIG. 1), the central precursor to 3-methyl-but-2-enoyl-CoA, 3-methyl-2-oxo-butanoate, is converted to 3-methyl-2-hydroxy-butanoate by a 2-hydroxyacyl dehydrogenase classified, for example, under EC 1.1.1.272, EC 1.1.1.345 or EC 1.1.1.28; followed by conversion to 3-methyl-2-hydroxybutanoyl-CoA by a CoA transferase classified, for example, under EC 2.8.3.- such as the gene product of GctAB or a CoA-ligase classified, for example, under EC 6.2.1.2; followed by conversion to 3-methyl-but-2-enoyl-CoA by a 2-hydroxy-acyl-CoA dehydratase such as the gene product of HadBC and the initiator HadI, or HgdAB and the initiator HgdC; followed by conversion to 3-methyl-3-hydroxy-butanoyl-CoA by an enoyl-CoA hydratase classified, for example, under EC 4.2.1.119 such as the gene product of phaJ or MaoC, or classified, for example, under EC 4.2.1.17 such as the gene product of YsiB; followed by conversion to 3-methyl-3-hydroxy-butanoate by a thioesterase classified, for example, under EC 3.1.2.- such as the gene product of tesA, tesB, or YciA, or a CoA-transferase classified, for example, under EC 2.8.3.- such as the gene product of GctAB; followed by conversion to isobutene by a mevalonate diphosphate decarboxylase classified, for example, under EC 4.1.1.33. The thioesterase encoded by YciA, has broad substrate specificity, hydrolysing a number of branch chain fatty acids such as isobutyryl-CoA, isovaleryl-CoA, as well as 3-hydroxy-3-methylglutaryl-CoA (Zhuang et al., *Biochemistry*, 2008, 47, 2789-2796).

In some embodiments, 3-methyl-2-oxobutanoate is synthesized from pyruvate, by conversion of pyruvate to 2-acetolactate by an acetolactate synthase classified, for example, under EC 2.2.1.6 such as the gene product of ilvB or ilvN; followed by conversion to 2,3-dihydroxyisovalerate by a dihydroxyisovalerate dehydrogenase classified, for example, under EC 1.1.1.86 such as the gene product of ilvC; followed by conversion to 3-methyl-2-oxo-butanoate by a 2,3-dihydroxyisovalerate dehydratase classified, for example, under EC 4.2.1.9 such as the gene product of ilvD.

In some embodiments (FIG. 2), the central precursor to 3-methyl-but-2-enoyl-CoA, 4-methyl-2-oxo-pentanoate, is converted to 3-methylbutanoate by a 4-methyl-2-oxo-pentanoate dehydrogenase complex classified, for example, under EC 1.2.1.- such as the gene products of pdhD, bfmBB, bfmBAA and bfmBAB, or classified under EC 1.2.7.7; followed by conversion to 3-methylbut-2-enoyl-CoA by an isovaleryl-CoA/acyl-CoA dehydrogenase classified, for example, under EC 1.3.8.4 such as the gene product of liuA or acdH; followed by conversion to 3-methyl-3-hydroxy-butanoyl-CoA by a (R)-specific enoyl-CoA hydratase classified, for example, under EC 4.2.1.119 such as the gene product of phca or MaoC, or classified, for example, under EC 4.2.1.17 such as the gene product of YsiB; followed by conversion to 3-methyl-3-hydroxy-butanoate by a thioesterase classified, for example, under EC 3.1.2.- such as the gene product of tesA, tesB, or YciA; followed by conversion to isobutene by a mevalonate diphosphate decarboxylase classified under EC 4.1.1.33.

In some embodiments (FIG. 2), the central precursor to 3-methyl-but-2-enoyl-CoA, 4-methyl-2-oxo-pentanoate, is converted to 3-methylbutanal by an indolepyruvate decarboxylase classified, for example, under EC 4.1.1.74 or EC 4.1.1.43; followed by conversion to 3-methyl-butanoate by a phenylacetaldehyde dehydrogenase classified, for example, under EC 1.2.1.5 or EC 1.2.1.39 such as the gene product of padA; followed by conversion to 3-methyl-butanoyl-CoA by a CoA-ligase classified, for example, under EC 6.2.1.2; followed by conversion to 3-methyl-but-2-enoyl-CoA by an isovaleryl-CoA/acyl-CoA dehydrogenase classified, for example, under EC 1.3.8.4 such as the gene product of liuA or acdH; followed by conversion to 3-methyl-3-hydroxy-butanoyl-CoA by a (R)-specific enoyl-CoA hydratase classified, for example, under EC 4.2.1.119 such as the gene product of phaJ or MaoC, or classified, for example, under EC 4.2.1.17 such as the gene product of YsiB; followed by conversion to 3-methyl-3-hydroxy-butanoate by a thioesterase classified, for example, under EC 3.1.2.- such as the gene product of tesA, tesB, or YciA; followed by conversion to isobutene by a mevalonate diphosphate decarboxylase classified under EC 4.1.1.33.

Figure 2:
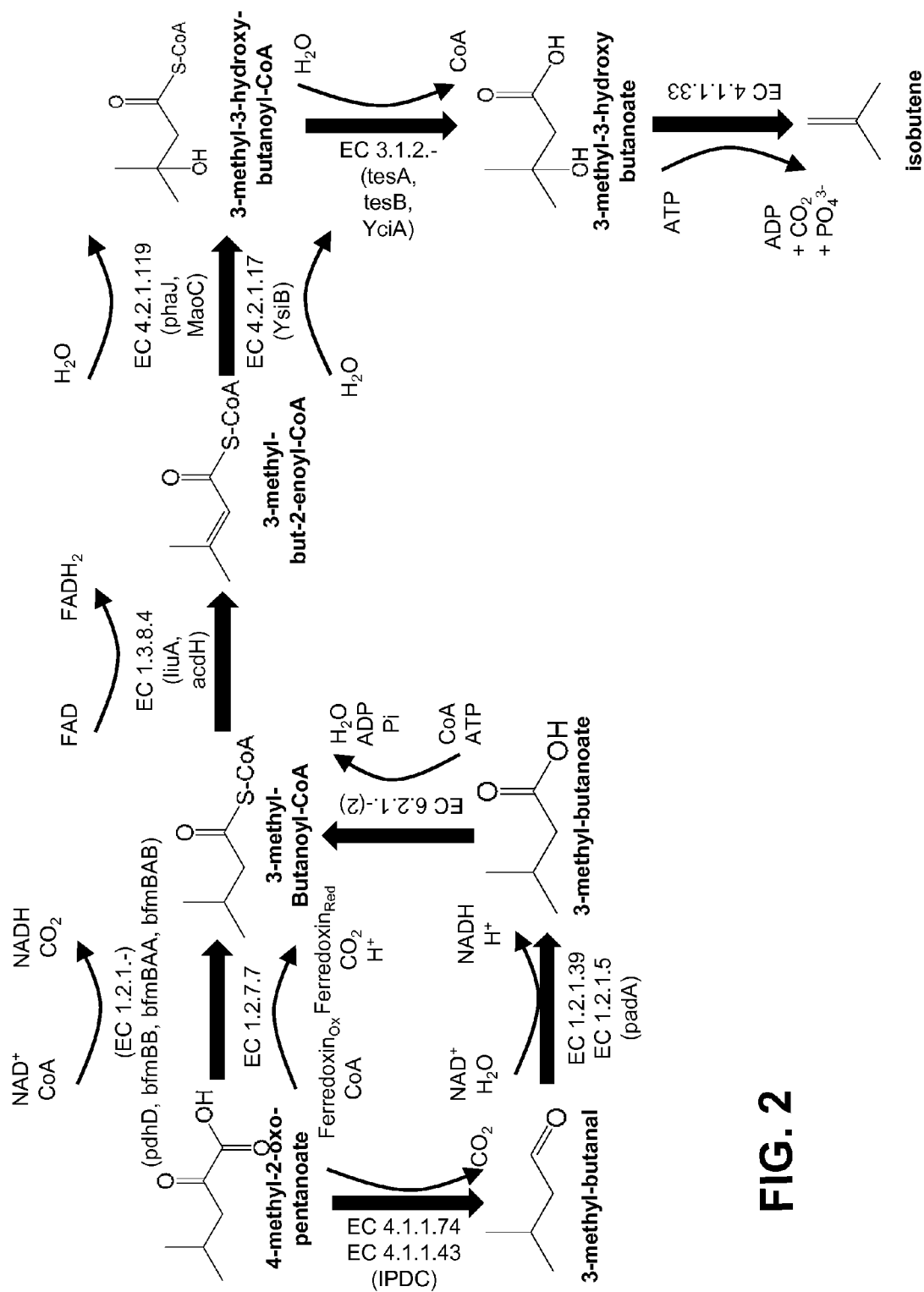
FIG. 2 is a schematic of exemplary biochemical pathways leading to isobutene using 4-methyl-2-oxopentanoate as a central precursor.

In some embodiments, the nucleic acids encoding the enzymes of the pathways described in FIG. 1 or 2 are introduced into a host microorganism that is either a prokaryote or eukaryote.

In some embodiments, the host microorganism is a prokaryote from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis*, or from the genus *Rhodococcus* such as *Rhodococcus equi*.

In some embodiments, the host microorganism is a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

In some embodiments, isobutene is biosynthesized in a recombinant host using a fermentation strategy that can include anaerobic, micro-aerobic or aerobic cultivation of the recombinant host.

In some embodiments, isobutene is biosynthesized in a recombinant host under nutrient limiting conditions such as nitrogen, phosphate or oxygen limitation.

In some embodiments, isobutene is biosynthesized in a recombinant host using a fermentation strategy that uses an alternate final electron acceptor to oxygen such as nitrate.

In some embodiments, a cell retention strategy using, for example, ceramic hollow fiber membranes can be employed to achieve and maintain a high cell density during either fed batch or continuous fermentation in the synthesis of isobutene.

In some embodiments, the biological feedstock can be, can include, or can derive from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166, 1801-1813; Yang et al., *Biotechnology for Biofuels,* 2012, 5:13; Meijnen et al., *Appl. Microbiol. Biotechnol.,* 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology,* 2011, 155, 2011, 293-298; Martin and Prather, *Journal of Biotechnology,* 2009, 139, 61-67).

The efficient catabolism of lignin-derived aromatic compounds such benzoate analogues has been demonstrated in several microorganisms such as *Pseudomonas putida, Cupriavidus necator* (Bugg et al., *Current Opinion in Biotechnology,* 2011, 22, 394-400; Pérez-Pantoja et al., *FEMS Microbiol. Rev.,* 2008, 32, 736-794).

The efficient utilization of agricultural waste, such as olive mill waste water has been demonstrated in several microorganisms, including *Yarrowia lipolytica* (Papanikolaou et al., *Bioresour. Technol.,* 2008, 99(7), 2419-2428).

The efficient utilization of fermentable sugars such as monosaccharides and disaccharides derived from cellulosic, hemicellulosic, cane and beet molasses, cassava, corn and other argricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology,* 2003, 104, 155-172; Wee et al., *Food Technol. Biotechnol.,* 2006, 44(2), 163-172; Ohashi et al., *Journal of Bioscience and Bioengineering,* 1999, 87(5), 647-654).

The efficient utilization of furfural, derived from a variety of agricultural lignocellulosic sources, has been demonstrated for *Cupriavidus necator* (Li et al., *Biodegradation,* 2011, 22, 1215-1225).

In some embodiments, the non-biological feedstock can be or can derive from natural gas, syngas, $CO_2/H_2$, methanol, ethanol, non-volatile residue (NVR) or a caustic wash waste stream from cyclohexane oxidation processes.

The efficient catabolism of methanol has been demonstrated for the methylotropic yeast *Pichia pastoris*.

The efficient catabolism of ethanol has been demonstrated for *Clostridium kluyveri* (Seedorf et al., *Proc. Natl. Acad. Sci. USA,* 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society,* 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology,* 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology,* 1986, 52(1), 152-156).

In some embodiments, substantially pure cultures of recombinant host microorganisms are provided. As used herein, a "substantially pure culture" of a recombinant host microorganism is a culture of that microorganism in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein can be the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined herein can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to isobutene.

Attenuation strategies include, but are not limited to, the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to isobutene.

In some embodiments using hosts that naturally accumulate polyhydroxyalkanoates, the polymer synthase enzymes can be attenuated in the host strain.

In some embodiments requiring the intracellular availability of acetyl-CoA for isobutene synthesis, a host that is deficient (e.g., attenuated level of activity) in one or more enzymes in the acetate synthesis pathway can be used. For example, a host that is deficient in a phosphotransacetylase (encoded by the pta gene) can be used (Shen et al., *Appl. Environ. Microbio.,* 2011, 77(9), 2905-2915).

In some embodiments requiring the intracellular availability of acetyl-CoA or pyruvate for isobutene synthesis, an enzyme degrading pyruvate to lactate can be attenuated (such as the gene product of ldhA) (Shen et al., *Appl. Environ. Microbiol.,* 2011, 77(9), 2905-2915).

In some embodiments requiring the intracellular availability of pyruvate for isobutene synthesis, an enzyme that degrades phophoenolpyruvate to succinate, such as the gene product of frdBC, can be attenuated (see, e.g., Shen et al., 2011, supra).

In some embodiments requiring the intracellular availability of pyruvate for isobutene synthesis, a gene encoding an enzyme degrading acetyl-CoA to ethanol, such as the gene product of adhE, can be attenuated (Shen et al., 2011, supra).

In some embodiments, where pathways require excess NADPH co-factor in the synthesis of isobutene, a gene encoding a puridine nucleotide transhydrogenase such as UdhA can be overexpressed in the host organism (Brigham et al., *Advanced Biofuels and Bioproducts,* 2012, Chapter 39, 1065-1090).

In some embodiments, where pathways require excess NADPH co-factor in the synthesis of isobutene, a glyceraldehyde-3P-dehydrogenase gene such as GapN can be overexpressed in the host organism (Brigham et al., 2012, supra).

In some embodiments, where pathways require excess NADPH co-factor in the synthesis of isobutene, a malic enzyme gene such as macA or maeB can be overexpressed in the host organism (Brigham et al., 2012, supra).

In some embodiments, where pathways require excess NADPH co-factor in the synthesis of isobutene, a glucose-6-phosphate dehydrogenase gene such as zwf can be overexpressed in the host organism (Lim et al., *Journal of Bioscience and Bioengineering*, 2002, 93(6), 543-549).

In some embodiments, where pathways require excess NADPH co-factor in the synthesis of isobutene, a gene encoding a fructose 1,6 diphosphatase such as fbp can be overexpressed in the host (Becker et al., *Journal of Biotechnology*, 2007, 132, 99-109).

In some embodiments, a feedback inhibition resistant mutant of an acetolactate synthase classified, for example, under EC 2.2.1.6, such as mutants of ilvB and/or ilvN that are resistant to feedback inhibition by branch chain amino acids, can be overexpressed in the host.

In some embodiments, acetolactate synthase can be expressed under a promoter not subject to genetic repression by branch-chain amino acids (e.g., valine, leucine, or isoleucine).

In some embodiments, the branch chain amino acid transaminase encoded by ilvE is attenuated.

In some embodiments, the efflux of isobutene across the cell membrane to the extracellular media can be enhanced or amplified by genetically engineering structural modifications to the cell membrane or increasing any associated transporter activity for isobutene.

Producing Isobutene Using a Recombinant Host

Typically, isobutene is produced by providing a host microorganism and culturing the provided microorganism with a culture medium containing a suitable carbon source as described above. In general, the culture media and/or culture conditions can be such that the microorganisms grow to an adequate density and produce isobutene efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of isobutene. Once produced, any method can be used to isolate isobutene. For example, isobutene can be recovered from the fermenter off-gas stream as a volatile product as the boiling point of isobutene is −6.9° C. At a typical fermentation temperature of approximately 30° C., isobutene boils off from the broth, stripped by the gas flow rate through the broth for recovery from the off-gas. Isobutene can be selectively adsorbed onto, for example, an adsorbent and separated from the other off-gas components. Membrane separation technology may also be employed to separate isobutene from the other off-gas compounds. Isobutene may desorbed from the adsorbent using, for example, nitrogen and condensed at low temperature and high pressure.

Example

Enzyme Activity of R-Specific Enoyl-CoA Hydratase Accepting 3-Methyl-3-Hydroxybutanoyl-CoA as Substrate A C-terminal His-tagged phaJ gene from *Aeromonas punctata*, which encodes a R-specific enoyl-CoA hydratase (SEQ ID NO:2, see FIG. 3) was cloned into a pE23a expression vector under the T7 promoter. The expression vector was transformed into a BL21[DE3] *E. coli* host. The resulting recombinant *E. coli* strain was cultivated at 30° C. in a 1 L shake flask culture containing 100 mL Luria Broth media, with shaking at 200 rpm. The culture was induced using 1 mM IPTG for 2 hours.

The pellet from each of the induced shake flask cultures was harvested by centrifugation. Each pellet was resuspended in 20 mM HEPES (pH=7.2 [−]), 1 mM PMSF and 29 units benzonase, and lysed via sonication. The cell debris was separated from the supernatant via centrifugation and filtered using a 0.2 µm filter. The phaJ enzyme was purified from the supernatant using Ni-affinity chromatography and concentrated to 1.25 mg/mL.

Figure 6:
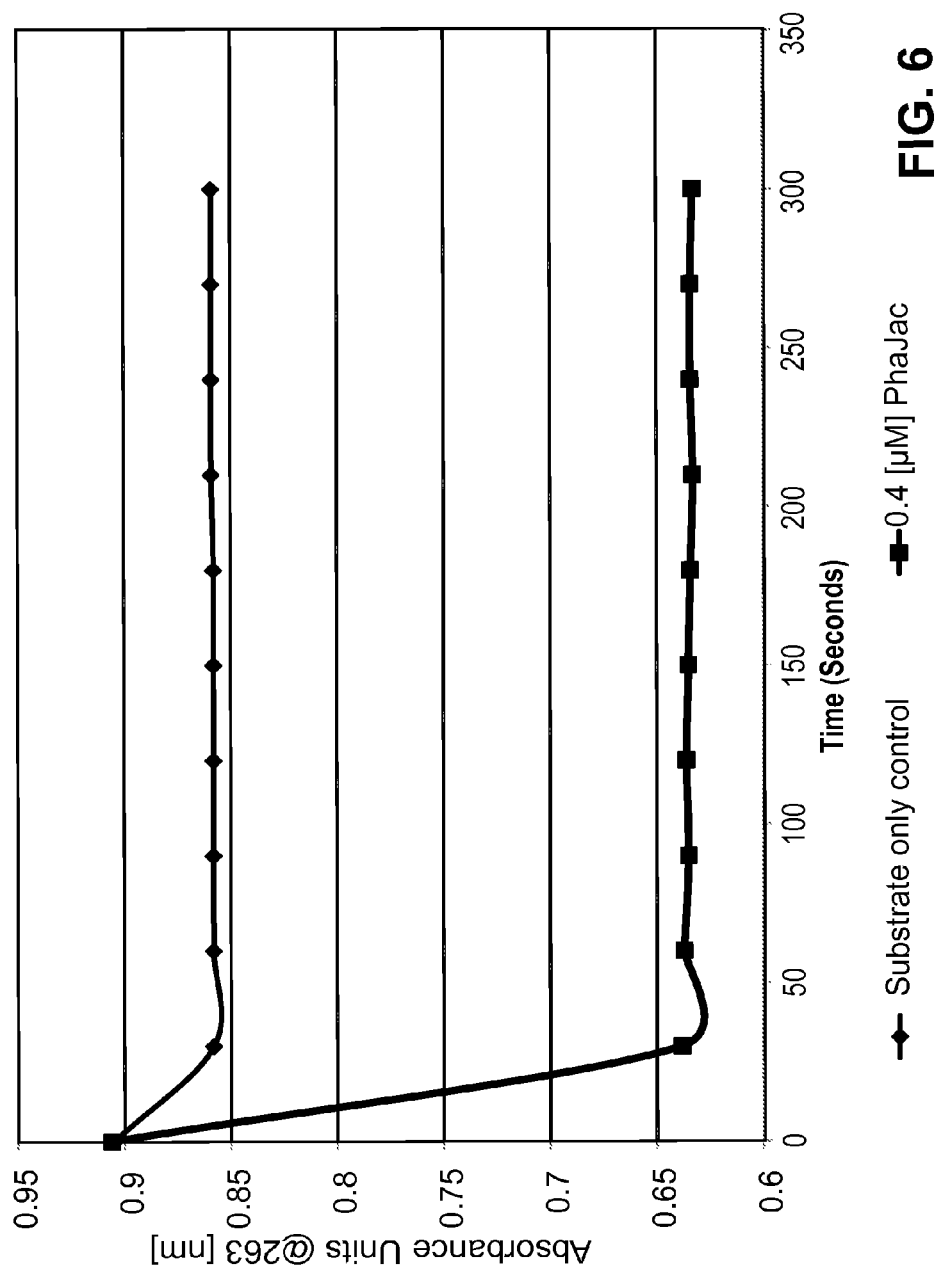
FIG. 6 is a graph of the absorbance units of crotonyl-CoA (substrate) over time in a spectrophotometric enzyme assay in the forward (hydrating) direction for an enoyl-CoA hydratase encoded by phaJ.

The native enzyme activity assay in the forward (hydration) direction was undertaken in a buffer composed of 10 mM ammonium acetate (pH=8) and 1 mM of crotonyl-CoA (also known as 2-butenoyl-CoA) (Sigma-Aldrich) at 30° C. The enzyme activity assay reaction was initiated by adding 0.4 µM of purified enoyl-CoA hydratase to the assay buffer containing the substrate. The enoyl-CoA hydratase accepted crotonyl-CoA as substrate as confirmed via spectrophotometry at 263 nm at 30° C. The substrate only control showed minimal spontaneous hydration of crotonyl-CoA as determined by spectrophotometry at 263 nm. See FIG. 6.

The native enzyme activity assay in the reverse (dehydration) direction was undertaken in a buffer composed of 10 mM ammonium acetate (pH=8) and 1 mM of racemic 3-hydroxybutanoyl-CoA. The enzyme activity assay reaction was initiated by adding 5 µM of purified enoyl-CoA hydratase to the assay buffer containing the substrate and incubated at 30° C. for 1 hour. The enoyl-CoA hydratase accepted 3-hydroxybutanoyl-CoA as substrate as confirmed via LC-MS. The substrate only control showed negligible spontaneous dehydration of 3-hydroxybutanoyl-CoA. As demonstrated previously (Lan and Liao, *Proc. Natl. Acad. Sci. USA*, 2012, 109(16), 6018-6023), the enoyl-CoA hydratase encoded by phaJ is reversible, though favors the forward (hydration) direction. See FIG. 7.

The non-native enzyme activity assay in the reverse (dehydration) direction was undertaken in a buffer composed of 10 mM ammonium acetate (pH=8) and 1 mM of 3-methyl-3-hydroxybutanoyl-CoA. The enzyme activity assay reaction was initiated by adding 5 µM of purified enoyl-CoA hydratase to the assay buffer containing the substrate and incubated at 30° C. for 1 hour. The enzyme encoded by phaJ accepted 3-methyl-3-hydroxybutanoyl-CoA as substrate as confirmed via LC-MS. The substrate only control showed no spontaneous dehydration of 3-methyl-3-hydroxybutanoyl-CoA. See FIG. 8.

The enoyl-CoA hydratase encoded by phaJ from *Aeromonas punctata* accepted 3-methyl-3-hydroxybutanoyl-CoA as substrate in the dehydration direction. Given the reversibility of the enzyme reaction and the favored hydration direction, the enoyl-CoA hydratase encoded by phaJ from *Aeromonas punctata* accepts 3-methyl-but-2-enoyl-CoA as substrate.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for synthesizing isobutene, said method comprising:
   (a) culturing a recombinant host cell genetically engineered to synthesize isobutene via said method in a culture medium in the presence of a fermentable carbon source, said recombinant host cell comprising exogenous nucleic acids encoding polypeptides having the activities of:
   (i) a 2-hydroxyacyl-CoA dehydratase, wherein said polypeptide has 2-hydroxyacyl-CoA dehydratase activity and comprises the amino acid sequences selected from the group consisting of SEQ ID NO:5, SEQ ID NO:6, SEQ ID NO:8 and SEQ ID NO:9;
   (ii) an (R)-specific enoyl-CoA hydratase, wherein said polypeptide has (R)-specific enoyl-CoA hydratase activity and comprises the amino acid sequences selected from the group consisting of SEQ ID NO:1, SEQ ID NO:2 and SEQ ID NO:3;
   (iii) a thioesterase classified under 3.1.2.-; and
   (iv) a mevalonate diphosphate decarboxylase classified under 4.1.1.33;
   (b) enzymatically dehydrating 3-methyl-2-hydroxy-butanoyl-CoA to form 3-methyl-but-2-enoyl-CoA using said polypeptide having the 2-hydroxyacyl-CoA dehydratase activity in said host cell;
   (c) enzymatically hydrating the 3-methyl-but-2-enoyl-CoA to form 3-methyl-3-hydroxy butanoyl-CoA using said polypeptide having the (R)-specific enoyl-CoA hydratase activity in said host cell;
   (d) enzymatically converting 3-methyl-3-hydroxy butanoyl-CoA to 3-methyl-3-hydroxybutanoate using said polypeptide having the thioesterase activity in said host cell; and
   (e) enzymatically converting 3-methyl-3-hydroxybutanoate to isobutene using said polypeptide having the mevalonate diphosphate decarboxylase activity in said host cell.

2. The method of claim 1, wherein said 2-hydroxyacyl-CoA dehydratase is the gene products:
   activator of 2-hydroxyisocaproyl-CoA dehydratase (HadI) and 2-hydroxyisocaproyl-CoA dehydratase (HadBC); or
   activator of (R)-hydroxyglutaryl-CoA dehydratase B (HgdC) and 2-hydoxyglutaryl-CoA dehydratase B (hgdB) protein precursor (HgdAB).

3. The method of claim 1, where the host is a prokaryote.

4. The method according to claim 3, where the prokaryotic host is from the genus selected from the group consisting of *Escherichia; Clostridia; Corynebacteria; Cupriavidus; Pseudomonas; Delftia acidovorans, Bacillus; Lactobacillus; Lactococcus* and *Rhodococcus*.

5. The method according to claim 1, where the fermentable carbon source is a feedstock selected from cellulose, lignin, levulinic acid, triglycerides, glycerol, fatty acids, agricultural waste, condensed distillers' solubles and municipal waste.

6. The method according to claim 1, where the fermentable carbon source is a feedstock selected from natural gas, syngas, $CO_2/H_2$, methanol and ethanol.

7. The method of claim 1, wherein the host is a eukaryote.

8. The method according to claim 7, where the eukaryotic host is from the genus selected from the group consisting of *Aspergillus; Saccharomyces; Pichia; Yarrowia; Issatchenkia; Debaryomyces; Arxula* and *Kluyveromyces*.

9. The method according to claim 1, where the fermentable carbon source is a feedstock selected from monosaccharides, disaccharides, lignocellulose, hemicellulose and formic acid.

* * * * *

```
                              SEQUENCE LISTING

<160> NUMBER OF SEQ ID NOS: 12

<210> SEQ ID NO 1
<211> LENGTH: 156
<212> TYPE: PRT
<213> ORGANISM: Pseudomonas aeruginosa

<400> SEQUENCE: 1

Met Ser Gln Val Gln Asn Ile Pro Tyr Ala Glu Leu Glu Val Gly Gln
 1               5                  10                  15

Lys Ala Glu Tyr Thr Ser Ser Ile Ala Glu Arg Asp Leu Gln Leu Phe
                20                  25                  30

Ala Ala Val Ser Gly Asp Arg Asn Pro Val His Leu Asp Ala Ala Tyr
            35                  40                  45

Ala Ala Thr Thr Gln Phe Lys Glu Arg Ile Ala His Gly Met Leu Ser
        50                  55                  60

Gly Ala Leu Ile Ser Ala Ala Ile Ala Thr Val Leu Pro Gly Pro Gly
65                  70                  75                  80

Thr Ile Tyr Leu Gly Gln Thr Leu Arg Phe Thr Arg Pro Val Lys Leu
                85                  90                  95

Gly Asp Asp Leu Lys Val Glu Leu Glu Val Leu Glu Lys Leu Pro Lys
            100                 105                 110

Asn Arg Val Arg Met Ala Thr Arg Val Phe Asn Gln Ala Gly Lys Gln
        115                 120                 125

Val Val Asp Gly Glu Ala Glu Ile Met Ala Pro Glu Glu Lys Leu Ser
130                 135                 140

Val Glu Leu Ala Glu Leu Pro Pro Ile Ser Ile Gly
145                 150                 155

<210> SEQ ID NO 2
<211> LENGTH: 134
<212> TYPE: PRT
<213> ORGANISM: Aeromonas punctata

<400> SEQUENCE: 2

Met Ser Ala Gln Ser Leu Glu Val Gly Gln Lys Ala Arg Leu Ser Lys
 1               5                  10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
            35                  40                  45

Glu Arg Pro Ile Val His Gly Met Leu Leu Ala Ser Leu Phe Ser Gly
        50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
            100                 105                 110

Thr Thr Arg Ile Phe Thr Gln Gly Gly Ala Leu Ala Val Thr Gly Glu
        115                 120                 125
```

```
Ala Val Val Lys Leu Pro
        130
```

<210> SEQ ID NO 3
<211> LENGTH: 156
<212> TYPE: PRT
<213> ORGANISM: Pseudomonas putida

<400> SEQUENCE: 3

```
Met Ser Gln Val Thr Asn Thr Pro Tyr Glu Ala Leu Glu Val Gly Gln
 1               5                  10                  15

Lys Ala Glu Tyr Lys Lys Ser Val Glu Glu Arg Asp Ile Gln Leu Phe
            20                  25                  30

Ala Ala Met Ser Gly Asp His Asn Pro Val His Leu Asp Ala Glu Phe
        35                  40                  45

Ala Ala Lys Ser Met Phe Arg Glu Arg Ile Ala His Gly Met Phe Ser
    50                  55                  60

Gly Ala Leu Ile Ser Ala Val Ala Cys Thr Leu Pro Gly Pro Gly
 65                 70                  75                  80

Thr Ile Tyr Leu Gly Gln Gln Met Ser Phe Gln Lys Pro Val Lys Ile
                85                  90                  95

Gly Asp Thr Leu Thr Val Arg Leu Glu Ile Leu Glu Lys Leu Pro Lys
            100                 105                 110

Phe Lys Val Arg Ile Ala Thr Asn Val Tyr Asn Gln Asn Asp Glu Leu
        115                 120                 125

Val Val Ala Gly Glu Ala Glu Ile Leu Ala Pro Arg Lys Gln Gln Thr
    130                 135                 140

Val Glu Leu Val Ser Pro Pro Asn Phe Val Ala Ser
145                 150                 155
```

<210> SEQ ID NO 4
<211> LENGTH: 258
<212> TYPE: PRT
<213> ORGANISM: Bacillus subtilis

<400> SEQUENCE: 4

```
Met Asn Ala Ile Ser Leu Ala Val Asp Gln Phe Val Ala Val Leu Thr
 1               5                  10                  15

Ile His Asn Pro Pro Ala Asn Ala Leu Ser Ser Arg Ile Leu Glu Glu
            20                  25                  30

Leu Ser Ser Cys Leu Asp Gln Cys Glu Thr Asp Ala Gly Val Arg Ser
        35                  40                  45

Ile Ile Ile His Gly Glu Gly Arg Phe Phe Ser Ala Gly Ala Asp Ile
    50                  55                  60

Lys Glu Phe Thr Ser Leu Lys Gly Asn Glu Asp Ser Ser Leu Leu Ala
 65                 70                  75                  80

Glu Arg Gly Gln Gln Leu Met Glu Arg Ile Glu Ser Phe Pro Lys Pro
                85                  90                  95

Ile Ile Ala Ala Ile His Gly Ala Ala Leu Gly Gly Gly Leu Glu Leu
            100                 105                 110

Ala Met Ala Cys His Ile Arg Ile Ala Ala Glu Asp Ala Lys Leu Gly
        115                 120                 125

Leu Pro Glu Leu Asn Leu Gly Ile Ile Pro Gly Phe Ala Gly Thr Gln
    130                 135                 140

Arg Leu Pro Arg Tyr Val Gly Thr Ala Lys Ala Leu Glu Leu Ile Gly
145                 150                 155                 160
```

```
Ser Gly Glu Pro Ile Ser Gly Lys Glu Ala Leu Asp Leu Gly Leu Val
            165                 170                 175

Ser Ile Gly Ala Lys Asp Glu Ala Glu Val Ile Glu Lys Ala Lys Ala
        180                 185                 190

Leu Ala Ala Lys Phe Ala Glu Lys Ser Pro Gln Thr Leu Ala Ser Leu
            195                 200                 205

Leu Glu Leu Leu Tyr Ser Asn Lys Val Tyr Ser Tyr Glu Gly Ser Leu
        210                 215                 220

Lys Leu Glu Ala Lys Arg Phe Gly Glu Ala Phe Glu Ser Glu Asp Ala
225                 230                 235                 240

Lys Glu Gly Ile Gln Ala Phe Leu Glu Lys Arg Lys Pro Gln Phe Lys
            245                 250                 255

Gly Glu

<210> SEQ ID NO 5
<211> LENGTH: 408
<212> TYPE: PRT
<213> ORGANISM: Clostridium difficile

<400> SEQUENCE: 5

Met Ser Glu Lys Lys Glu Ala Arg Val Val Ile Asn Asp Leu Leu Ala
 1               5                  10                  15

Glu Gln Tyr Ala Asn Ala Phe Lys Ala Lys Glu Glu Gly Arg Pro Val
            20                  25                  30

Gly Trp Ser Thr Ser Val Phe Pro Gln Glu Leu Ala Glu Val Phe Asp
        35                  40                  45

Leu Asn Val Leu Tyr Pro Glu Asn Gln Ala Ala Gly Val Ala Ala Lys
    50                  55                  60

Lys Gly Ser Leu Glu Leu Cys Glu Ile Ala Glu Ser Lys Gly Tyr Ser
65                  70                  75                  80

Ile Asp Leu Cys Ala Tyr Ala Arg Thr Asn Phe Gly Leu Leu Glu Asn
            85                  90                  95

Gly Gly Cys Glu Ala Leu Asp Met Pro Ala Pro Asp Phe Leu Leu Cys
            100                 105                 110

Cys Asn Asn Ile Cys Asn Gln Val Ile Lys Trp Tyr Glu Asn Ile Ser
        115                 120                 125

Arg Glu Leu Asp Ile Pro Leu Ile Met Ile Asp Thr Thr Phe Asn Asn
130                 135                 140

Glu Asp Glu Val Thr Gln Ser Arg Ile Asp Tyr Ile Lys Ala Gln Phe
145                 150                 155                 160

Glu Glu Ala Ile Lys Gln Leu Glu Ile Ile Ser Gly Lys Lys Phe Asp
            165                 170                 175

Pro Lys Lys Phe Glu Glu Val Met Lys Ile Ser Ala Glu Asn Gly Arg
        180                 185                 190

Leu Trp Lys Tyr Ser Met Ser Leu Pro Ala Asp Ser Ser Pro Ser Pro
    195                 200                 205

Met Asn Gly Phe Asp Leu Phe Thr Tyr Met Ala Val Ile Val Cys Ala
    210                 215                 220

Arg Gly Lys Lys Glu Thr Thr Glu Ala Phe Lys Leu Leu Ile Glu Glu
225                 230                 235                 240

Leu Glu Asp Asn Met Lys Thr Gly Lys Ser Ser Phe Arg Gly Glu Glu
            245                 250                 255

Lys Tyr Arg Ile Met Met Glu Gly Ile Pro Cys Trp Pro Tyr Ile Gly
        260                 265                 270
```

```
Tyr Lys Met Lys Thr Leu Ala Lys Phe Gly Val Asn Met Thr Gly Ser
            275                 280                 285

Val Tyr Pro His Ala Trp Ala Leu Gln Tyr Glu Val Asn Asp Leu Asp
        290                 295                 300

Gly Met Ala Val Ala Tyr Ser Thr Met Phe Asn Asn Val Asn Leu Asp
305                 310                 315                 320

Arg Met Thr Lys Tyr Arg Val Asp Ser Leu Val Glu Gly Lys Cys Asp
                325                 330                 335

Gly Ala Phe Tyr His Met Asn Arg Ser Cys Lys Leu Met Ser Leu Ile
                340                 345                 350

Gln Tyr Glu Met Gln Arg Arg Ala Ala Glu Thr Gly Leu Pro Tyr
                355                 360                 365

Ala Gly Phe Asp Gly Asp Gln Ala Asp Pro Arg Ala Phe Thr Asn Ala
        370                 375                 380

Gln Phe Glu Thr Arg Ile Gln Gly Leu Val Glu Val Met Glu Glu Arg
385                 390                 395                 400

Lys Lys Leu Asn Arg Gly Glu Ile
                405

<210> SEQ ID NO 6
<211> LENGTH: 375
<212> TYPE: PRT
<213> ORGANISM: Clostridium difficile

<400> SEQUENCE: 6

Met Glu Ala Ile Leu Ser Lys Met Lys Glu Val Val Glu Asn Pro Asn
1               5                   10                  15

Ala Ala Val Lys Lys Tyr Lys Ser Glu Thr Gly Lys Lys Ala Ile Gly
            20                  25                  30

Cys Phe Pro Val Tyr Cys Pro Glu Glu Ile Ile His Ala Ala Gly Met
        35                  40                  45

Leu Pro Val Gly Ile Trp Gly Gly Gln Thr Glu Leu Asp Leu Ala Lys
    50                  55                  60

Gln Tyr Phe Pro Ala Phe Ala Cys Ser Ile Met Gln Ser Cys Leu Glu
65              70                  75                  80

Tyr Gly Leu Lys Gly Ala Tyr Asp Glu Leu Ser Gly Val Ile Ile Pro
                85                  90                  95

Gly Met Cys Asp Thr Leu Ile Cys Leu Gly Gln Asn Trp Lys Ser Ala
            100                 105                 110

Val Pro His Ile Lys Tyr Ile Ser Leu Val His Pro Gln Asn Arg Lys
        115                 120                 125

Leu Glu Ala Gly Val Tyr Leu Ile Ser Glu Tyr Lys Gly Val Lys
    130                 135                 140

Arg Glu Leu Glu Glu Ile Cys Gly Tyr Glu Ile Glu Glu Ala Lys Ile
145                 150                 155                 160

His Glu Ser Ile Glu Val Tyr Asn Glu His Arg Lys Thr Met Arg Asp
                165                 170                 175

Phe Val Glu Val Ala Tyr Lys His Ser Asn Thr Ile Lys Pro Ser Ile
            180                 185                 190

Arg Ser Leu Val Ile Lys Ser Gly Phe Phe Met Arg Lys Glu Glu His
        195                 200                 205

Thr Glu Leu Val Lys Asp Leu Ile Ala Lys Leu Asn Ala Met Pro Glu
    210                 215                 220

Glu Val Cys Ser Gly Lys Lys Val Leu Leu Thr Gly Ile Leu Ala Asp
225                 230                 235                 240
```

```
Ser Lys Asp Ile Leu Asp Ile Leu Glu Asp Asn Asn Ile Ser Val Val
            245                 250                 255

Ala Asp Asp Leu Ala Gln Glu Thr Arg Gln Phe Arg Thr Asp Val Pro
            260                 265                 270

Ala Gly Asp Asp Ala Leu Glu Arg Leu Ala Arg Gln Trp Ser Asn Ile
            275                 280                 285

Glu Gly Cys Ser Leu Ala Tyr Asp Pro Lys Lys Arg Gly Ser Leu
            290                 295                 300

Ile Val Asp Glu Val Lys Lys Asp Ile Asp Gly Val Ile Phe Cys
305                 310                 315                 320

Met Met Lys Phe Cys Asp Pro Glu Glu Tyr Asp Tyr Pro Leu Val Arg
            325                 330                 335

Lys Asp Ile Glu Asp Ser Gly Ile Pro Thr Leu Tyr Val Glu Ile Asp
            340                 345                 350

Gln Gln Thr Gln Asn Asn Glu Gln Ala Arg Thr Arg Ile Gln Thr Phe
            355                 360                 365

Ala Glu Met Met Ser Leu Ala
            370                 375

<210> SEQ ID NO 7
<211> LENGTH: 266
<212> TYPE: PRT
<213> ORGANISM: Clostridium difficile

<400> SEQUENCE: 7

Met Tyr Thr Met Gly Leu Asp Ile Gly Ser Thr Ala Ser Lys Gly Val
  1               5                  10                  15

Ile Leu Lys Asn Gly Glu Asp Ile Val Ala Ser Glu Thr Ile Ser Ser
             20                  25                  30

Gly Thr Gly Thr Thr Gly Pro Ser Arg Val Leu Glu Lys Leu Tyr Gly
         35                  40                  45

Lys Thr Gly Leu Ala Arg Glu Asp Ile Lys Lys Val Val Thr Gly
     50                  55                  60

Tyr Gly Arg Met Asn Tyr Ser Asp Ala Asp Lys Gln Ile Ser Glu Leu
65                  70                  75                  80

Ser Cys His Ala Arg Gly Val Asn Phe Ile Ile Pro Glu Thr Arg Thr
                85                  90                  95

Ile Ile Asp Ile Gly Gly Gln Asp Ala Lys Val Leu Lys Leu Asp Asn
            100                 105                 110

Asn Gly Arg Leu Leu Asn Phe Leu Met Asn Asp Lys Cys Ala Ala Gly
            115                 120                 125

Thr Gly Arg Phe Leu Asp Val Met Ala Lys Ile Glu Val Asp Val
            130                 135                 140

Ser Glu Leu Gly Ser Ile Ser Met Asn Ser Gln Asn Glu Val Ser Ile
145                 150                 155                 160

Ser Ser Thr Cys Thr Val Phe Ala Glu Ser Glu Val Ile Ser His Leu
                165                 170                 175

Ser Glu Asn Ala Lys Ile Glu Asp Ile Val Ala Gly Ile His Thr Ser
            180                 185                 190

Val Ala Lys Arg Val Ser Ser Leu Val Lys Arg Ile Gly Val Gln Arg
            195                 200                 205

Asn Val Val Met Val Gly Gly Val Ala Arg Asn Ser Gly Ile Val Arg
            210                 215                 220

Ala Met Ala Arg Glu Ile Asn Thr Glu Ile Ile Val Pro Asp Ile Pro
```

```
                225                 230                 235                 240
        Gln Leu Thr Gly Ala Leu Gly Ala Ala Leu Tyr Ala Phe Asp Glu Ala
                        245                 250                 255

Lys Glu Ser Gln Lys Glu Val Lys Asn Ile
                        260                 265

<210> SEQ ID NO 8
<211> LENGTH: 477
<212> TYPE: PRT
<213> ORGANISM: Acidaminococcus fermentans

<400> SEQUENCE: 8

Met Pro Lys Thr Val Ser Pro Gly Val Gln Ala Leu Arg Asp Val Val
         1               5                  10                  15

Glu Lys Val Tyr Arg Glu Leu Arg Glu Ala Lys Glu Arg Gly Glu Lys
                        20                  25                  30

Val Gly Trp Ser Ser Ser Lys Phe Pro Cys Glu Leu Ala Glu Ser Phe
                        35                  40                  45

Gly Leu His Val Gly Tyr Pro Glu Asn Gln Ala Ala Gly Ile Ala Ala
                50                  55                  60

Asn Arg Asp Gly Glu Val Met Cys Gln Ala Ala Glu Asp Ile Gly Tyr
        65                  70                  75                  80

Asp Asn Asp Ile Cys Gly Tyr Ala Arg Ile Ser Leu Ala Tyr Ala Ala
                        85                  90                  95

Gly Phe Arg Gly Ala Asn Lys Met Asp Lys Asp Gly Asn Tyr Val Ile
                        100                 105                 110

Asn Pro His Ser Gly Lys Gln Met Lys Asp Ala Asn Gly Lys Lys Val
                        115                 120                 125

Phe Asp Ala Asp Gly Lys Pro Val Ile Asp Pro Lys Thr Leu Lys Pro
                130                 135                 140

Phe Ala Thr Thr Asp Asn Ile Tyr Glu Ile Ala Ala Leu Pro Glu Gly
        145                 150                 155                 160

Glu Glu Lys Thr Arg Arg Gln Asn Ala Leu His Lys Tyr Arg Gln Met
                        165                 170                 175

Thr Met Pro Met Pro Asp Phe Val Leu Cys Cys Asn Asn Ile Cys Asn
                        180                 185                 190

Cys Met Thr Lys Trp Tyr Glu Asp Ile Ala Arg Arg His Asn Ile Pro
                        195                 200                 205

Leu Ile Met Ile Asp Val Pro Tyr Asn Glu Phe Asp His Val Asn Glu
                210                 215                 220

Ala Asn Val Lys Tyr Ile Arg Ser Gln Leu Asp Thr Ala Ile Arg Gln
        225                 230                 235                 240

Met Glu Glu Ile Thr Gly Lys Lys Phe Asp Glu Asp Lys Phe Glu Gln
                        245                 250                 255

Cys Cys Gln Asn Ala Asn Arg Thr Ala Lys Ala Trp Leu Lys Val Cys
                        260                 265                 270

Asp Tyr Leu Gln Tyr Lys Pro Ala Pro Phe Asn Gly Phe Asp Leu Phe
                        275                 280                 285

Asn His Met Ala Asp Val Val Thr Ala Arg Gly Arg Val Glu Ala Ala
                290                 295                 300

Glu Ala Phe Glu Leu Leu Ala Lys Glu Leu Glu Gln His Val Lys Glu
        305                 310                 315                 320

Gly Thr Thr Thr Ala Pro Phe Lys Glu Gln His Arg Ile Met Phe Glu
                        325                 330                 335
```

```
Gly Ile Pro Cys Trp Pro Lys Leu Pro Asn Leu Phe Lys Pro Leu Lys
            340                 345                 350

Ala Asn Gly Leu Asn Ile Thr Gly Val Val Tyr Ala Pro Ala Phe Gly
        355                 360                 365

Phe Val Tyr Asn Asn Leu Asp Glu Leu Val Lys Ala Tyr Cys Lys Ala
    370                 375                 380

Pro Asn Ser Val Ser Ile Glu Gln Gly Val Ala Trp Arg Glu Gly Leu
385                 390                 395                 400

Ile Arg Asp Asn Lys Val Asp Gly Val Leu Val His Tyr Asn Arg Ser
                405                 410                 415

Cys Lys Pro Trp Ser Gly Tyr Met Pro Glu Met Gln Arg Arg Phe Thr
            420                 425                 430

Lys Asp Met Gly Ile Pro Thr Ala Gly Phe Asp Gly Asp Gln Ala Asp
        435                 440                 445

Pro Arg Asn Phe Asn Ala Ala Gln Tyr Glu Thr Arg Val Gln Gly Leu
    450                 455                 460

Val Glu Ala Met Glu Ala Asn Asp Glu Lys Lys Gly Lys
465                 470                 475

<210> SEQ ID NO 9
<211> LENGTH: 379
<212> TYPE: PRT
<213> ORGANISM: Acidaminococcus fermentans

<400> SEQUENCE: 9

Met Ala Ile Ser Ala Leu Ile Glu Glu Phe Gln Lys Val Ser Ala Ser
 1               5                  10                  15

Pro Lys Thr Met Leu Ala Lys Tyr Lys Ala Gln Gly Lys Lys Ala Ile
                20                  25                  30

Gly Cys Leu Pro Tyr Tyr Val Pro Glu Glu Leu Val Tyr Ala Ala Gly
            35                  40                  45

Met Val Pro Met Gly Val Trp Gly Cys Asn Gly Lys Gln Glu Val Arg
        50                  55                  60

Ser Lys Glu Tyr Cys Ala Ser Phe Tyr Cys Thr Ile Ala Gln Gln Ser
65                  70                  75                  80

Leu Glu Met Leu Leu Asp Gly Thr Leu Asp Gly Leu Asp Gly Ile Ile
                85                  90                  95

Thr Pro Val Leu Cys Asp Thr Leu Arg Pro Met Ser Gln Asn Phe Lys
            100                 105                 110

Val Ala Met Lys Asp Lys Met Pro Val Ile Phe Leu Ala His Pro Gln
        115                 120                 125

Val Arg Gln Asn Ala Ala Gly Lys Gln Phe Thr Tyr Asp Ala Tyr Ser
    130                 135                 140

Glu Val Lys Gly His Leu Glu Glu Ile Cys Gly His Glu Ile Thr Asn
145                 150                 155                 160

Asp Ala Ile Leu Asp Ala Ile Lys Val Tyr Asn Lys Ser Arg Ala Ala
                165                 170                 175

Arg Arg Glu Phe Cys Lys Leu Ala Asn Glu His Pro Asp Leu Ile Pro
            180                 185                 190

Ala Ser Val Arg Ala Thr Val Leu Arg Ala Ala Tyr Phe Met Leu Lys
        195                 200                 205

Asp Glu Tyr Thr Glu Lys Leu Glu Glu Leu Asn Lys Glu Leu Ala Ala
    210                 215                 220

Ala Pro Ala Gly Lys Phe Asp Gly His Lys Val Val Ser Gly Ile
225                 230                 235                 240
```

```
Ile Tyr Asn Met Pro Gly Ile Leu Lys Ala Met Asp Asn Lys Leu
                245                 250                 255

Ala Ile Ala Ala Asp Asp Cys Ala Tyr Glu Ser Arg Ser Phe Ala Val
            260                 265                 270

Asp Ala Pro Glu Asp Leu Asp Asn Gly Leu Gln Ala Leu Ala Val Gln
            275                 280                 285

Phe Ser Lys Gln Lys Asn Asp Val Leu Leu Tyr Asp Pro Glu Phe Ala
        290                 295                 300

Lys Asn Thr Arg Ser Glu His Val Cys Asn Leu Val Lys Glu Ser Gly
305                 310                 315                 320

Ala Glu Gly Leu Ile Val Phe Met Met Gln Phe Cys Asp Pro Glu Glu
                325                 330                 335

Met Glu Tyr Pro Asp Leu Lys Lys Ala Leu Asp Ala His His Ile Pro
            340                 345                 350

His Val Lys Ile Gly Val Asp Gln Met Thr Arg Asp Phe Gly Gln Ala
        355                 360                 365

Gln Thr Ala Leu Glu Ala Phe Ala Glu Ser Leu
        370                 375

<210> SEQ ID NO 10
<211> LENGTH: 260
<212> TYPE: PRT
<213> ORGANISM: Acidaminococcus fermentans

<400> SEQUENCE: 10

Met Ser Ile Tyr Thr Leu Gly Ile Asp Val Gly Ser Thr Ala Ser Lys
1               5                   10                  15

Cys Ile Ile Leu Lys Asp Gly Lys Glu Ile Val Ala Lys Ser Leu Val
            20                  25                  30

Ala Val Gly Thr Gly Thr Ser Gly Pro Ala Arg Ser Ile Ser Glu Val
        35                  40                  45

Leu Glu Asn Ala His Met Lys Lys Glu Asp Met Ala Phe Thr Leu Ala
    50                  55                  60

Thr Gly Tyr Gly Arg Asn Ser Leu Glu Gly Ile Ala Asp Lys Gln Met
65                  70                  75                  80

Ser Glu Leu Ser Cys His Ala Met Gly Ala Ser Phe Ile Trp Pro Asn
                85                  90                  95

Val His Thr Val Ile Asp Ile Gly Gly Gln Asp Val Lys Val Ile His
            100                 105                 110

Val Glu Asn Gly Thr Met Thr Asn Phe Gln Met Asn Asp Lys Cys Ala
        115                 120                 125

Ala Gly Thr Gly Arg Phe Leu Asp Val Met Ala Asn Ile Leu Glu Val
    130                 135                 140

Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ile Ala Gly Ile His
            180                 185                 190

Arg Ser Val Ala Ser Arg Val Ile Gly Leu Ala Asn Arg Val Gly Ile
        195                 200                 205

Val Lys Asp Val Val Met Thr Gly Gly Val Ala Gln Asn Tyr Gly Val
    210                 215                 220

Arg Gly Ala Leu Glu Glu Gly Leu Gly Val Glu Ile Lys Thr Ser Pro
```

```
                225                 230                 235                 240
Leu Ala Gln Tyr Asn Gly Ala Leu Gly Ala Ala Leu Tyr Ala Tyr Lys
                245                 250                 255

Lys Ala Ala Lys
        260

<210> SEQ ID NO 11
<211> LENGTH: 387
<212> TYPE: PRT
<213> ORGANISM: Pseudomonas aeruginosa

<400> SEQUENCE: 11

Met Thr Tyr Pro Ser Leu Asn Phe Ala Leu Gly Glu Thr Ile Asp Met
  1               5                  10                  15

Leu Arg Asp Gln Val Arg Gly Phe Val Ala Ala Glu Leu Gln Pro Arg
                 20                  25                  30

Ala Ala Gln Ile Asp Gln Asp Asn Gln Phe Pro Met Asp Met Trp Arg
             35                  40                  45

Lys Phe Gly Glu Met Gly Leu Leu Gly Ile Thr Val Asp Glu Glu Tyr
         50                  55                  60

Gly Gly Ser Ala Leu Gly Tyr Leu Ala His Ala Val Val Met Glu Glu
 65                  70                  75                  80

Ile Ser Arg Ala Ser Ala Ser Val Ala Leu Ser Tyr Gly Ala His Ser
                 85                  90                  95

Asn Leu Cys Val Asn Gln Ile Lys Arg Asn Gly Asn Ala Glu Gln Lys
            100                 105                 110

Ala Arg Tyr Leu Pro Ala Leu Val Ser Gly Glu His Ile Gly Ala Leu
        115                 120                 125

Ala Met Ser Glu Pro Asn Ala Gly Ser Asp Val Val Ser Met Lys Leu
    130                 135                 140

Arg Ala Asp Arg Val Gly Asp Arg Phe Val Leu Asn Gly Ser Lys Met
145                 150                 155                 160

Trp Ile Thr Asn Gly Pro Asp Ala His Thr Tyr Val Ile Tyr Ala Lys
                165                 170                 175

Thr Asp Ala Asp Lys Gly Ala His Gly Ile Thr Ala Phe Ile Val Glu
            180                 185                 190

Arg Asp Trp Lys Gly Phe Ser Arg Gly Pro Lys Leu Asp Lys Leu Gly
        195                 200                 205

Met Arg Gly Ser Asn Thr Cys Glu Leu Ile Phe Gln Asp Val Glu Val
    210                 215                 220

Pro Glu Glu Asn Val Leu Gly Ala Val Asn Gly Gly Val Lys Val Leu
225                 230                 235                 240

Met Ser Gly Leu Asp Tyr Glu Arg Val Val Leu Ser Gly Gly Pro Val
                245                 250                 255

Gly Ile Met Gln Ala Cys Met Asp Val Val Pro Tyr Ile His Asp
            260                 265                 270

Arg Arg Gln Phe Gly Gln Ser Ile Gly Glu Phe Gln Leu Val Gln Gly
        275                 280                 285

Lys Val Ala Asp Met Tyr Thr Ala Leu Asn Ala Ser Arg Ala Tyr Leu
    290                 295                 300

Tyr Ala Val Ala Ala Ala Cys Asp Arg Gly Glu Thr Thr Arg Lys Asp
305                 310                 315                 320

Ala Ala Gly Val Ile Leu Tyr Ser Ala Glu Arg Ala Thr Gln Met Ala
                325                 330                 335
```

```
Leu Asp Ala Ile Gln Ile Leu Gly Gly Asn Gly Tyr Ile Asn Glu Phe
                340                 345                 350

Pro Thr Gly Arg Leu Leu Arg Asp Ala Lys Leu Tyr Glu Ile Gly Ala
            355                 360                 365

Gly Thr Ser Glu Ile Arg Arg Met Leu Ile Gly Arg Glu Leu Phe Asn
        370                 375                 380

Glu Thr Arg
385

<210> SEQ ID NO 12
<211> LENGTH: 386
<212> TYPE: PRT
<213> ORGANISM: Streptomyces avermitilis

<400> SEQUENCE: 12

Met Asp His Arg Leu Thr Pro Glu Leu Glu Leu Arg Arg Thr Val
  1               5                  10                  15

Glu Glu Phe Ala His Asp Val Val Ala Pro Lys Ile Gly Asp Phe Tyr
                20                  25                  30

Glu Arg His Glu Phe Pro Tyr Glu Ile Val Arg Glu Met Gly Arg Met
            35                  40                  45

Gly Leu Phe Gly Leu Pro Phe Pro Glu Glu Tyr Gly Gly Met Gly Gly
        50                  55                  60

Asp Tyr Leu Ala Leu Gly Ile Ala Leu Glu Glu Leu Ala Arg Val Asp
 65                  70                  75                  80

Ser Ser Val Ala Ile Thr Leu Glu Ala Gly Val Ser Leu Gly Ala Met
                 85                  90                  95

Pro Ile His Leu Phe Gly Thr Asp Ala Gln Lys Ala Glu Trp Leu Pro
                100                 105                 110

Arg Leu Cys Ser Gly Glu Ile Leu Gly Ala Phe Gly Leu Thr Glu Pro
            115                 120                 125

Asp Gly Gly Ser Asp Ala Gly Ala Thr Arg Thr Thr Ala Arg Leu Asp
        130                 135                 140

Glu Ser Thr Asn Glu Trp Val Ile Asn Gly Thr Lys Cys Phe Ile Thr
145                 150                 155                 160

Asn Ser Gly Thr Asp Ile Thr Gly Leu Val Thr Val Thr Ala Val Thr
                165                 170                 175

Gly Arg Lys Pro Asp Gly Lys Pro Leu Ile Ser Ser Ile Ile Val Pro
            180                 185                 190

Ser Gly Thr Pro Gly Phe Thr Val Ala Ala Pro Tyr Ser Lys Val Gly
        195                 200                 205

Trp Asn Ala Ser Asp Thr Arg Glu Leu Ser Phe Ala Asp Val Arg Val
210                 215                 220

Pro Ala Ala Asn Leu Leu Gly Glu Gln Gly Arg Gly Tyr Ala Gln Phe
225                 230                 235                 240

Leu Arg Ile Leu Asp Glu Gly Arg Ile Ala Ile Ser Ala Leu Ala Thr
                245                 250                 255

Gly Leu Ala Gln Gly Cys Val Asp Glu Ser Val Lys Tyr Ala Gly Glu
            260                 265                 270

Arg His Ala Phe Gly Arg Asn Ile Gly Ala Tyr Gln Ala Ile Gln Phe
        275                 280                 285

Lys Ile Ala Asp Met Glu Met Lys Ala His Met Ala Arg Val Gly Trp
    290                 295                 300

Arg Asp Ala Ala Ser Arg Leu Val Ala Gly Glu Pro Phe Lys Lys Glu
305                 310                 315                 320
```

```
Ala Ala Ile Ala Lys Leu Tyr Ser Ser Thr Val Ala Val Asp Asn Ala
            325                 330                 335

Arg Glu Ala Thr Gln Ile His Gly Gly Tyr Gly Phe Met Asn Glu Tyr
            340                 345                 350

Pro Val Ala Arg Met Trp Arg Asp Ser Lys Ile Leu Glu Ile Gly Glu
            355                 360                 365

Gly Thr Ser Glu Val Gln Arg Met Leu Ile Ala Arg Glu Leu Gly Leu
            370                 375                 380

Val Gly
385
```